US012589219B2

(12) United States Patent
Tang et al.

(10) Patent No.: US 12,589,219 B2
(45) Date of Patent: Mar. 31, 2026

(54) STEERABLE SHEATH WITH VARIABLE CURVE SPAN

(71) Applicant: Biosense Webster (Israel) Ltd., Yokneam (IL)

(72) Inventors: Raymond Yue-sing Tang, Rosemead, CA (US); Mark T. Stanley, Seal Beach, CA (US); Christopher T. Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 725 days.

(21) Appl. No.: 16/821,159

(22) Filed: Mar. 17, 2020

(65) Prior Publication Data

US 2020/0222667 A1 Jul. 16, 2020

Related U.S. Application Data

(63) Continuation-in-part of application No. 14/715,013, filed on May 18, 2015, now Pat. No. 11,033,715.

(51) Int. Cl.
A61M 25/01 (2006.01)

(52) U.S. Cl.
CPC .... A61M 25/0102 (2013.01); A61M 25/0147 (2013.01); A61M 25/0138 (2013.01);
(Continued)

(58) Field of Classification Search
CPC .. A61M 2025/0161; A61M 2025/0175; A61M 2025/0177; A61M 2025/09083;
(Continued)

(56) References Cited

U.S. PATENT DOCUMENTS

| | | | |
|---|---|---|---|
| 4,742,817 A | | 5/1988 | Kawashima et al. |
| 4,935,017 A | * | 6/1990 | Sylvanowicz .. A61M 25/09025 |
| | | | 604/532 |

(Continued)

FOREIGN PATENT DOCUMENTS

| | | |
|---|---|---|
| CN | 103877663 A | 6/2014 |
| EP | 3 095 482 B1 | 2/2019 |

(Continued)

OTHER PUBLICATIONS

Chinese Office Action and Search Report dated May 26, 2020 for Application No. 201610329894.8, 8 pages.
(Continued)

*Primary Examiner* — Shefali D Patel

(74) *Attorney, Agent, or Firm* — FBT Gibbons LLP

(57) ABSTRACT

A guiding sheath assembly has a shaft that is operable to define more than one deflection curvature and defines a lumen to slidably receive a cardiovascular catheter. The guiding sheath assembly includes a proximal section, a distal section, and a stiffener member. The proximal section has a proximal shaft that defines a proximal lumen extending distally along a longitudinal axis to the distal section. The distal section has a distal shaft that defines a distal lumen that is configured to be biased (e.g., resiliently biased) laterally away from the longitudinal axis. The stiffener member is a rigid elongate member, such as an inner tubular member, that is configured to counteract the bias of the distal shaft. Longitudinal movement of the stiffener member relative to the distal section enables an operator to select and set a deflection curvature of the more than one deflection curvature.

15 Claims, 18 Drawing Sheets

(52) U.S. Cl.
CPC ............... *A61M 2025/0161* (2013.01); *A61M 2025/0175* (2013.01); *A61M 2025/0177* (2013.01)

(58) Field of Classification Search
CPC .......... A61M 25/0102; A61M 25/0138; A61M 25/0147
See application file for complete search history.

(56) References Cited

U.S. PATENT DOCUMENTS

| | | | |
|---|---|---|---|
| 5,168,864 | A | 12/1992 | Shockey |
| 5,195,968 | A | 3/1993 | Lundquist et al. |
| 5,199,950 | A | 4/1993 | Schmitt et al. |
| 5,345,937 | A * | 9/1994 | Middleman ....... A61M 25/0147 604/95.01 |
| 5,363,882 | A | 11/1994 | Chikama |
| 5,381,782 | A | 1/1995 | DeLaRama et al. |
| 5,441,483 | A | 8/1995 | Avitall |
| 5,487,757 | A | 1/1996 | Truckai et al. |
| 5,545,200 | A | 8/1996 | West et al. |
| 5,662,606 | A | 9/1997 | Cimino et al. |
| 5,664,580 | A | 9/1997 | Erickson et al. |
| 5,676,653 | A | 10/1997 | Taylor et al. |
| 5,715,817 | A | 2/1998 | Stevens-Wright et al. |
| 5,827,278 | A | 10/1998 | Webster, Jr. |
| 5,944,689 | A | 8/1999 | Houser et al. |
| 5,951,539 | A | 9/1999 | Nita et al. |
| 6,013,052 | A | 1/2000 | Durman et al. |
| 6,203,507 | B1 | 3/2001 | Wadsworth et al. |
| 6,585,718 | B2 | 7/2003 | Hayzelden et al. |
| 7,591,799 | B2 | 9/2009 | Selkee |
| 7,591,813 | B2 | 9/2009 | Levine et al. |
| 7,918,819 | B2 | 4/2011 | Karmarkar et al. |
| 8,617,087 | B2 | 12/2013 | Schultz et al. |
| 8,747,351 | B2 | 6/2014 | Schultz et al. |
| 9,050,010 | B2 | 6/2015 | Bui et al. |
| 10,046,141 | B2 | 8/2018 | Schultz |
| 11,033,715 | B2 | 6/2021 | Beeckler et al. |
| 11,896,780 | B2 | 2/2024 | Beeckler et al. |
| 2003/0187396 | A1 | 10/2003 | Ponzi |
| 2005/0021004 | A1 | 1/2005 | Cully et al. |
| 2006/0142732 | A1 | 6/2006 | Karmarkar et al. |
| 2016/0302819 | A1 | 10/2016 | Stulen et al. |
| 2016/0339207 | A1 | 11/2016 | Beeckler et al. |

FOREIGN PATENT DOCUMENTS

| | | |
|---|---|---|
| EP | 1033107 A1 | 9/2020 |
| JP | 8-71157 | 3/1996 |
| JP | 9-503931 | 4/1997 |
| JP | 2000-229084 A | 8/2000 |
| JP | 2003-144554 A | 5/2003 |
| JP | 2004-216150 A | 8/2004 |
| JP | 2009-511184 A | 3/2009 |
| JP | 2010-167101 A | 8/2010 |
| WO | WO 2004/045672 A2 | 6/2004 |
| WO | WO 2007/134872 A1 | 11/2007 |

OTHER PUBLICATIONS

European Search Report dated Oct. 4, 2016 for Application No. 16169970.7.

European Examination Report dated Nov. 2, 2017 for Application No. 16169970.7.

Japanese Office Action dated Feb. 25, 2020 for Application No. 2016-098617, 3 pages.

U.S. Appl. No. 17/145,446, entitled "Catheter with Adjustable Deflection," filed Jan. 11, 2021.

European Search Report for Application No. EP 21162748.4, dated Aug. 24, 2021, 10 pages.

Chinese Supplemental Search Report for Application No. 201610329894.8, dated Feb. 9, 2021, 2 pages.

Japanese Notification of Reasons for Refusal (Translation) for Application No. JP 2021-007090, dated Oct. 5, 2021, 4 pages.

Translation of Chinese Search Report for Application No. CN 201610329894.8, dated May 18, 2020, 3 pages.

Translation of Chinese First Office Action for Application No. CN 2016103298948, dated May 26, 2020, 5 pages.

Translation of Chinese Second Office Action for Application No. CN 2016103298948, dated Feb. 22, 2021, 6 pages.

Chinese First Office Action and Search Report dated Jun. 28, 2024, for Application No. 202110285366.8, 10 pages.

Chinese Second Office Action and Search Report dated Jan. 16, 2025, for Application No. 202110285366.8, 9 pages.

Japanese first Office Action dated Nov. 26, 2024, for Application No. 2021-042099, 12 pages.

* cited by examiner

STEERABLE SHEATH WITH VARIABLE CURVE SPAN

PRIORITY

This application is a continuation-in-part of U.S. patent application Ser. No. 14/715,013, entitled "Catheter with Adjustable Deflection," filed May 18, 2015, published as U.S. Pub. No. 2016/0339207 on Nov. 24, 2016, now U.S. Pat. No. 11,033,715, the disclosure of which is incorporated by reference herein.

FIELD OF INVENTION

This invention relates to electrophysiologic (EP) catheters, in particular, deflectable guide sheaths for use with EP catheters for mapping and/or ablation in the heart.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral vein, and then guided into the chamber of the heart which is of concern. Within the heart, the ability to control the exact position and orientation of the catheter tip is critical and largely determines how useful the catheter is.

Steerable (or deflectable) catheters are generally well-known. A typical catheter has an elongated catheter body, an intermediate deflection section and a distal tip section. The elongated catheter body extends through the patient's vasculature and the shorter intermediate deflection is steered or deflected to reach target tissue in responsive to a rocker arm on a control handle manipulated by an operator, e.g., an electrophysiologist. The catheter typically employs a single-lumened structure for the catheter body, and a multi-lumened structure for the intermediate deflection section which provides a dedicated lumen for each puller wire in order to facilitate deflection. The catheter is therefore a composite of different constructions and materials and consequently may not have uniform characteristics in flexibility, torsional stiffness, push-ability and/or rotational accuracy. Assembling puller wires and their respective compression coils, feeding distal portion of the puller wires through their dedicated lumens, and connecting the two structures all require extensive skilled manual labor. Moreover, inner walls of multi-lumened tubing occupy precious space within a catheter.

Because puller-wire-actuated deflection catheters rely on a junction of different flexibility/rigidity between the catheter body and the deflection section, the shape (including tightness of curvature) depends on the location of the junction in relation to the length of the catheter and/or location of the distal anchors of the puller wires. Accordingly, each of these catheters is designed and manufactured to provide one particular deflection curvature. Thus, depending on the specific heart anatomy of the patient in treatment, an electrophysiologist needs to correctly select a catheter curvature prior to start of the procedure, for example, a catheter with a "J" deflection curvature or a catheter with an "F" deflection curvature, to match the heart anatomy. A smaller heart may require a catheter with a tighter or smaller deflection. A larger heart may require a catheter with a looser or larger deflection.

Accordingly, it is desirable that a catheter have a more uniform construction throughout its entire length so that construction and assembly processes are simplified, and the catheter exhibit more uniformity in flexibility, torsional stiffness, push-ability and/or rotational accuracy along its entire length. It is also desirable that a catheter be adjustable to offer more than one deflection curvature in its catheter shaft.

In some procedures, it may be desirable to insert an electrode catheter into the cardiovascular system of a patient via a guiding sheath. The guiding sheath may facilitate access to targeted areas (e.g., the pulmonary vein) and may also facilitate sequential insertion and retraction of two or more electrode catheters (e.g., an electrophysiologic (EP) catheter first, followed by an ablation catheter). It may be further desirable to provide more than one deflection curvature in the guiding sheath.

While several catheter systems, guiding sheaths, and associated methods have been made and used, it is believed that no one prior to the inventors has made or used the invention described, illustrated, and claimed herein.

SUMMARY OF THE INVENTION

The present invention is directed to a catheter with a catheter shaft that has a more uniform construction throughout its length, including an elongated proximal section and a distal deflection section, and a catheter shaft that can adopt more than one deflection curvature. The catheter shaft includes a flexible outer tubular member, and a less flexible inner tubular member extending through the outer tubular member in the elongated proximal section of the catheter shaft, wherein the inner tubular member is afforded longitudinal movement relative to the outer tubular member. The catheter also includes at least one puller wire extending through the inner tubular member to deflect the distal deflection section of the catheter shaft, wherein longitudinal movement of the inner tubular member relative to the outer tubular member enables an operator to select and set a deflection curvature of the distal deflection section.

In some embodiments, the catheter has a catheter shaft with an elongated proximal section and a distal deflection section. The catheter shaft having an outer tubular member with a first center lumen. The catheter also has an inner tubular member having a second center lumen, wherein the inner tubular member extends through the first center lumen of the outer tubular member. The catheter further includes at least one puller wire extending through the second center lumen configured to deflect the distal deflection section In accordance with features of the present invention, the inner tubular member has a lesser flexibility and the outer tubular member has a greater flexibility so as to define a proximal end of the distal deflection section, and the inner tubular member is afforded longitudinal movement relative to the outer tubular member to enable an operator to adjust location of the proximal end along the length of the catheter shaft.

In more detailed embodiments, the outer tubular member has a coil construction, for example, a multi-layered coil construction, wherein each layer of the coil construction has a winding direction different from one or more adjacent layers. For example, an inner layer has a winding in a first direction, a middle layer has a winding in a second direction generally opposite to the first direction, and an outer layer has a winding in the first direction.

In more detailed embodiments, a distal end of the inner tubular member is even for symmetrical bidirectional deflection, or the distal end of the inner tubular member is uneven for asymmetrical bi-directional deflection. The uneven distal end may be sloped, notched or stepped.

In some embodiments, the catheter has a catheter shaft with a flexible multi-layered coil member, and a lumened stiffener member extending through the coil member, wherein a longitudinal position of the stiffener member relative to the coil member is adjustable to set a distal end of the stiffener member in defining a proximal end of the distal deflection section.

In some embodiments, the catheter includes a deflection curvature control handle with a handle body and a piston, wherein the piston is coupled for longitudinal movement with the stiffener member. The piston is adapted to releasably engage the handle body in multiple longitudinal configurations in defining correspondingly multiple locations at which the distal end of the stiffener member can be set.

In some embodiments, the catheter includes a pair of puller wire to provide bi-directional deflection curvatures of the distal section of the catheter shaft. In some embodiments, the distal end of the stiffener member is even to provide symmetrical bi-directional deflection curvatures, or alternatively, the distal end of the stiffener member is uneven to provide asymmetrical bi-directional deflection.

In some embodiments, opposing sections of the coil member along a diameter are fused or fixed together to provide in-plane deflection. For example, portions of adjacent coils along a diameter of the coil member are welded to promote flexion of the coil member in a plane generally perpendicular to the diameter and weld axis.

In some embodiments, a catheter includes a catheter shaft with a proximal section and a distal section. The catheter has a proximal shaft defining a proximal lumen extending distally along the longitudinal axis to a distal shaft defining a distal lumen. The distal shaft is biased in a first direction. The catheter has an inner tubular member having a central lumen. The inner tubular member extends through the proximal and distal lumens. The inner tubular member is configured to translate a member distal end distally through the proximal and distal lumens respectively. The inner tubular member has a lesser flexibility and the proximal and distal sections have a greater flexibility, with the distal section being laterally biased. The inner tubular member is afforded longitudinal movement relative to the proximal and distal shafts to enable an operator to adjust between various deflection curvatures.

In more detailed embodiments, a catheter includes a guide shaft assembly with a proximal section and a distal section. The guide shaft assembly has a proximal shaft defining a proximal lumen extending distally along the longitudinal axis to a distal shaft defining a distal lumen. The distal shaft is biased in a first direction. The guide sheath assembly further includes one or more inner elongate members disposed in one or more side lumens extending distally from the proximal shaft to the distal shaft. The one or more inner elongate members are affixed to a collar. The collar and inner elongate members act upon the distal section to selectively change between various deflection curvatures.

In more detailed embodiments, a guide sheath assembly includes a distal shaft with a first helical feature that mates with a second helical feature of the inner tubular member. Rotation of the second helical feature longitudinally translates the inner tubular member distally through the distal shaft to selectively change between various deflection curvatures.

In some embodiments, a guide sheath assembly includes a guide sheath including a collar, pull wire, pulley, and an inner tubular member. Simultaneous translation of the inner tubular member and pull wire selectively changes between various deflection curvatures.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "axial," and "longitudinal" also are used herein for reference to relative positions and directions. As well as rotational directional terms such as "clockwise" and "counterclockwise". However, surgical instruments are used in many orientations and positions, and these terms are not intended to be limiting and absolute.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Catheter with Variable Deflection Curvatures

Figure 1:
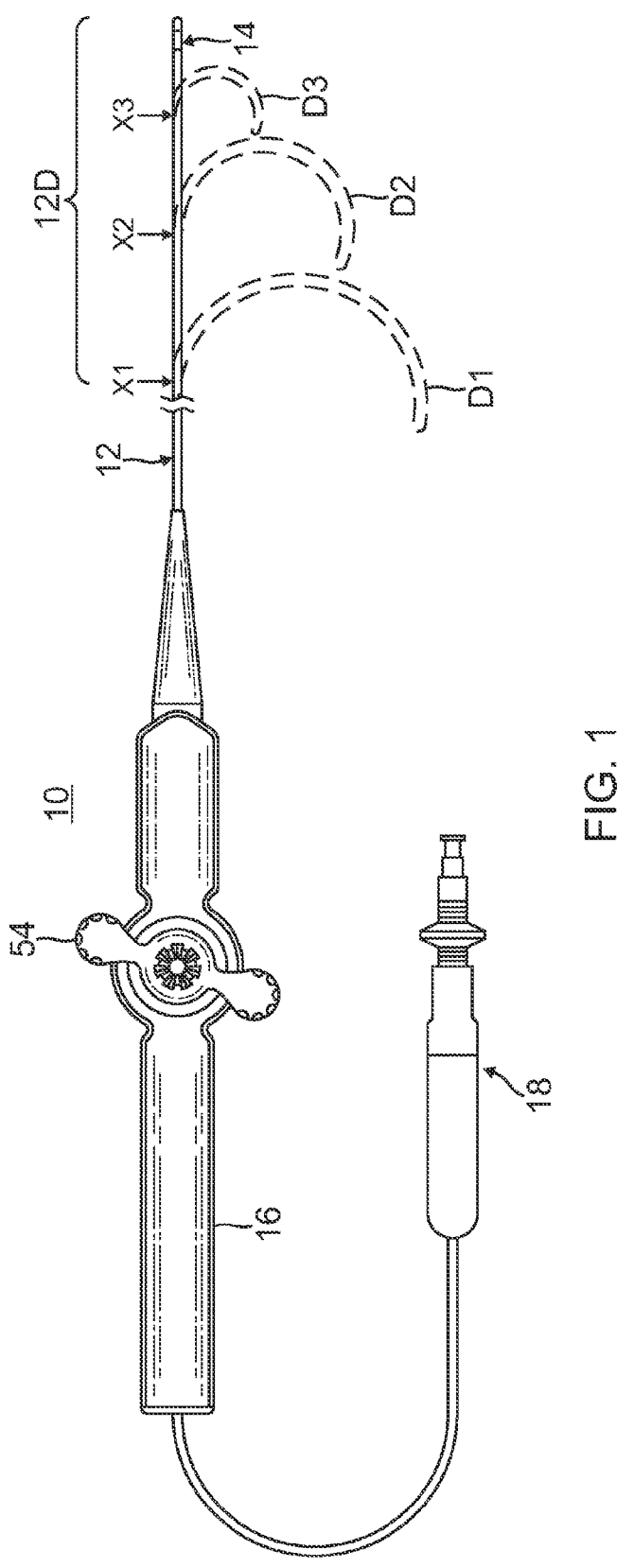
FIG. 1 is a top plan view of a catheter of the present invention, in accordance with some embodiments.

As shown in FIG. 1, a catheter 10 comprises an elongated catheter shaft 12, a distal section 14 with a distal tip electrode 15, a deflection rocker handle 16 attached to the proximal end of the catheter shaft 12 and a deflection curvature adjustment handle 18 proximal of the deflection rocker handle 16. In accordance with a feature of the present invention, the elongated catheter shaft 12 has an adjustable deflection section 12D which allows an operator user to vary and select the deflection curvature, as needed or desired, between multiple deflection curvatures, for example, D1, D2 and D3.

Figure 2A:
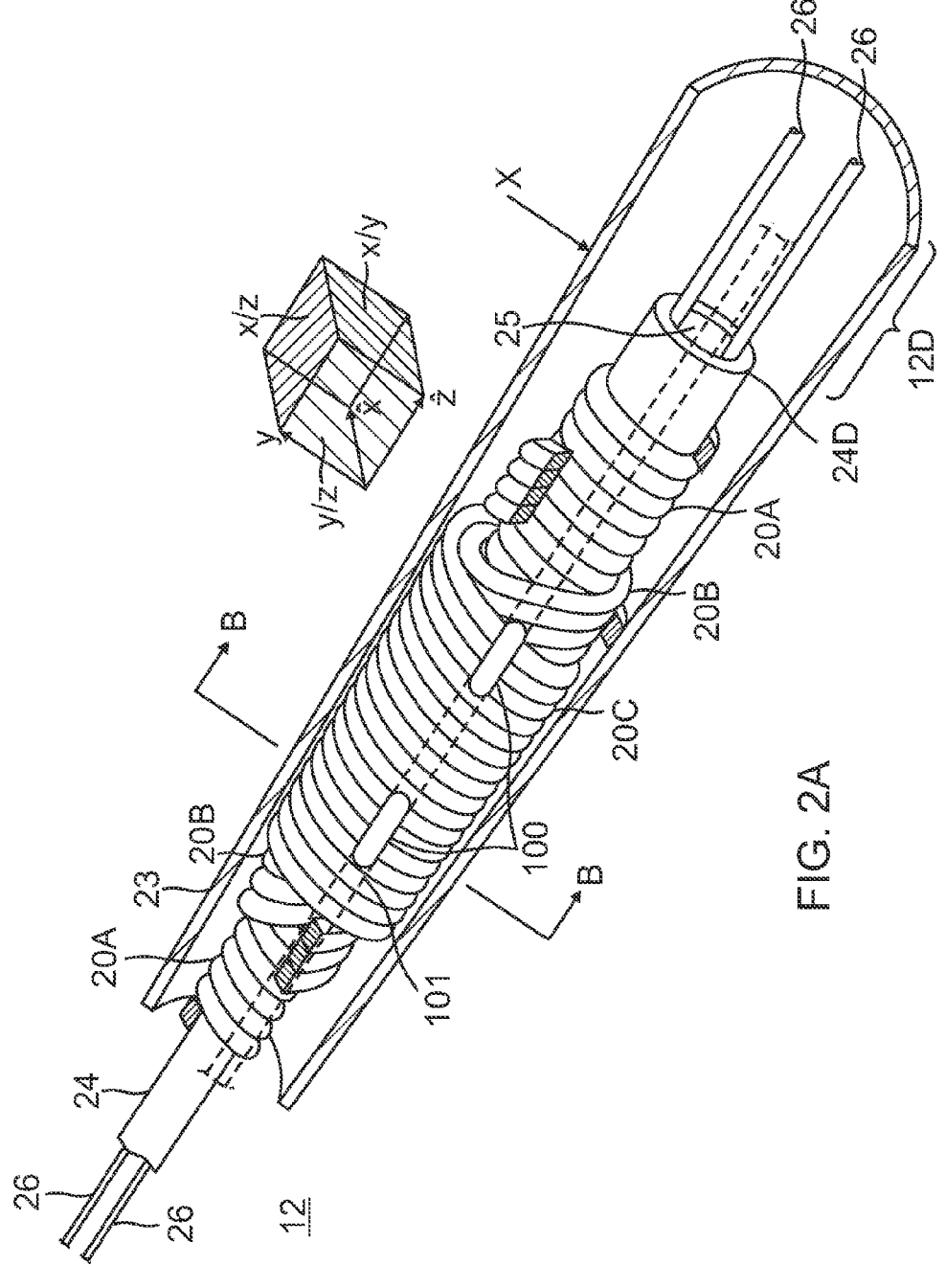
FIG. 2A is a perspective view of the catheter of FIG. 1, including a catheter shaft, with parts broken away.
Figure 2B:
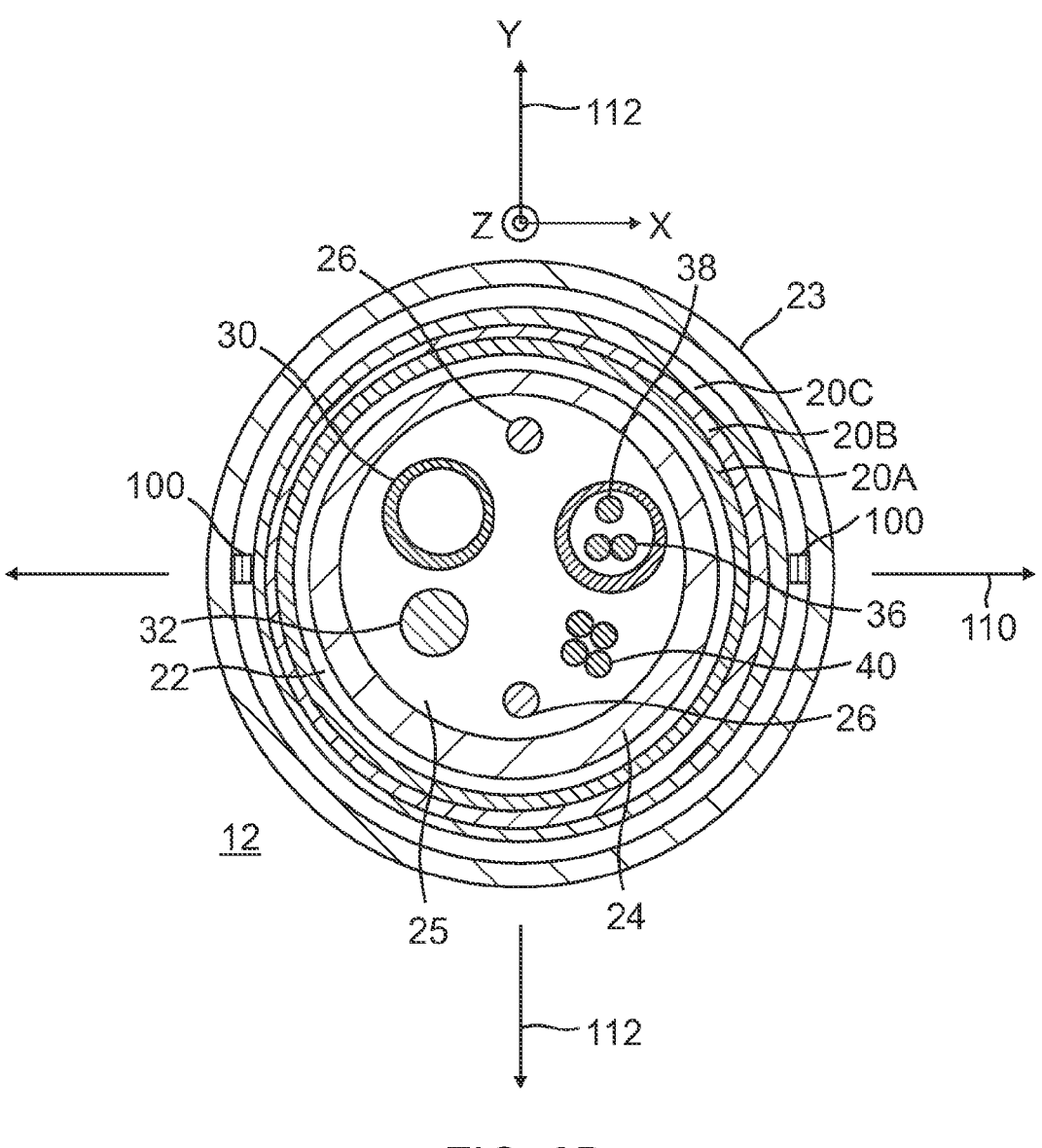
FIG. 2B is an end cross-sectional view of the catheter shaft of FIG. 2A, taken along line B-B.

With reference to FIGS. 2A and 2B, the catheter shaft 12 comprises an elongated tubular construction having a single, axial or central lumen 18. The catheter shaft 12 is flexible, i.e., bendable, but substantially non-compressible along its length. The catheter shaft 12 can be of any suitable construction and made of any suitable material. In some embodiments, the catheter shaft 12 comprises an outer multi-layered coil member 20 to provide flexibility, torsional stiffness, push-ability and rotational accuracy so that when the rocker handle 16 is rotated, the catheter shaft 12 and distal section 14 rotates in a corresponding manner.

In some embodiments, the multi-layered coil member 20 includes three layers of compression coils 20A, 20B and 20C, each coil strand or wire having a generally rectangular cross-section, and each coil being wound in a direction different from adjacent layer(s). For example, an inner coil; layer 20A and an outer coil layer 20C have a similar winding direction that is different from a winding direction of a middle layer 20B. In the illustrated embodiment of FIG. 2A, the winding direction of the inner coil layer 20A and the outer layer 20C is to the right of the Y axis and the winding direction of the middle layer 20B is generally opposite to the left of the Y axis. Suitable multi-layered coil members are available from Heraeus Medical Components, LLC and sold under the trademark TRIFLEX. An outer covering or shrink sleeve 23, for example, of any suitable biocompatible plastic such as polyurethane or PEBAX, is provided outside of the outer coil layer 20C to protect and provide a fluid-tight sealed interior of the catheter shaft 12.

The outer diameter of the catheter shaft 12 is not critical, but is preferably no more than about 12 french, more preferably about 7.5 french. The inner diameter of a central lumen 22 defined by the inner coil layer 20A is not critical, but is large enough so that the central lumen can accommodate at least an inner stiffener member 24 that extends through a proximal portion of the catheter shaft 12 and whose distal end 24D defines a proximal end X of the adjustable deflection section 12D of the catheter shaft 12.

The stiffener member 24 is an elongated lumened tubing that is afforded longitudinal movement relative to the multi-layered coil member 20. The stiffener member 24 has sufficient flexibility for maneuverability within a patient's vasculature but also sufficient rigidity to resist compression and deformity along its length within the central lumen 22 of the coil member 20 so to enable deflection of deflection section 12D in response to the one or more puller wires of the catheter 10. The stiffener member 24 has an outer diameter smaller than the inner diameter of the central lumen 22, and an inner diameter that is sufficiently large so that its central lumen 25 can accommodate various components, for example, one or more puller wires, one or more lead wires, irrigation tubing, and any other desired wires, cables or tubes.

To provide more flexibility in a distal portion of multi-layer coil member 20, a lesser number of coils can be used. In the illustrated embodiment of FIG. 3, inner coil layer 20A has a distal end proximal of the distal ends of the middle and outer coil layers 20B and 20C such that the distal portion of 20 has only two coils 20B and 20C instead of three. These distal portions of the coil layers 20B and 20C can be welded to form a tubular end portion 21 to allow for attachment for the puller wire 26 at welds W, as well as to lock the two coil layers together.

Figure 3:
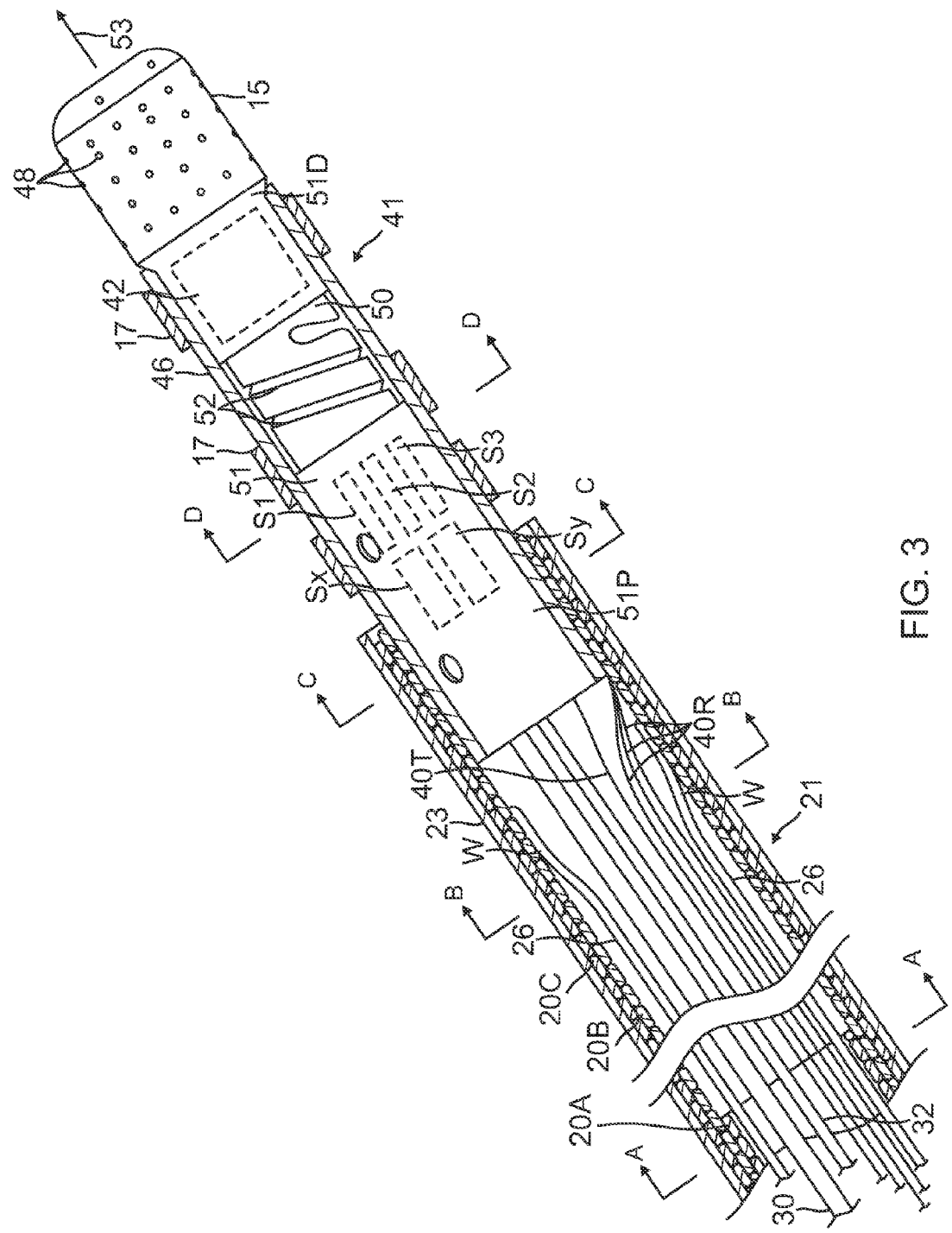
FIG. 3 is a perspective view of the catheter of FIG. 1, including a distal deflection section of the catheter shaft, and a distal tip section, with parts broken away.
Figures 3A, 3B:
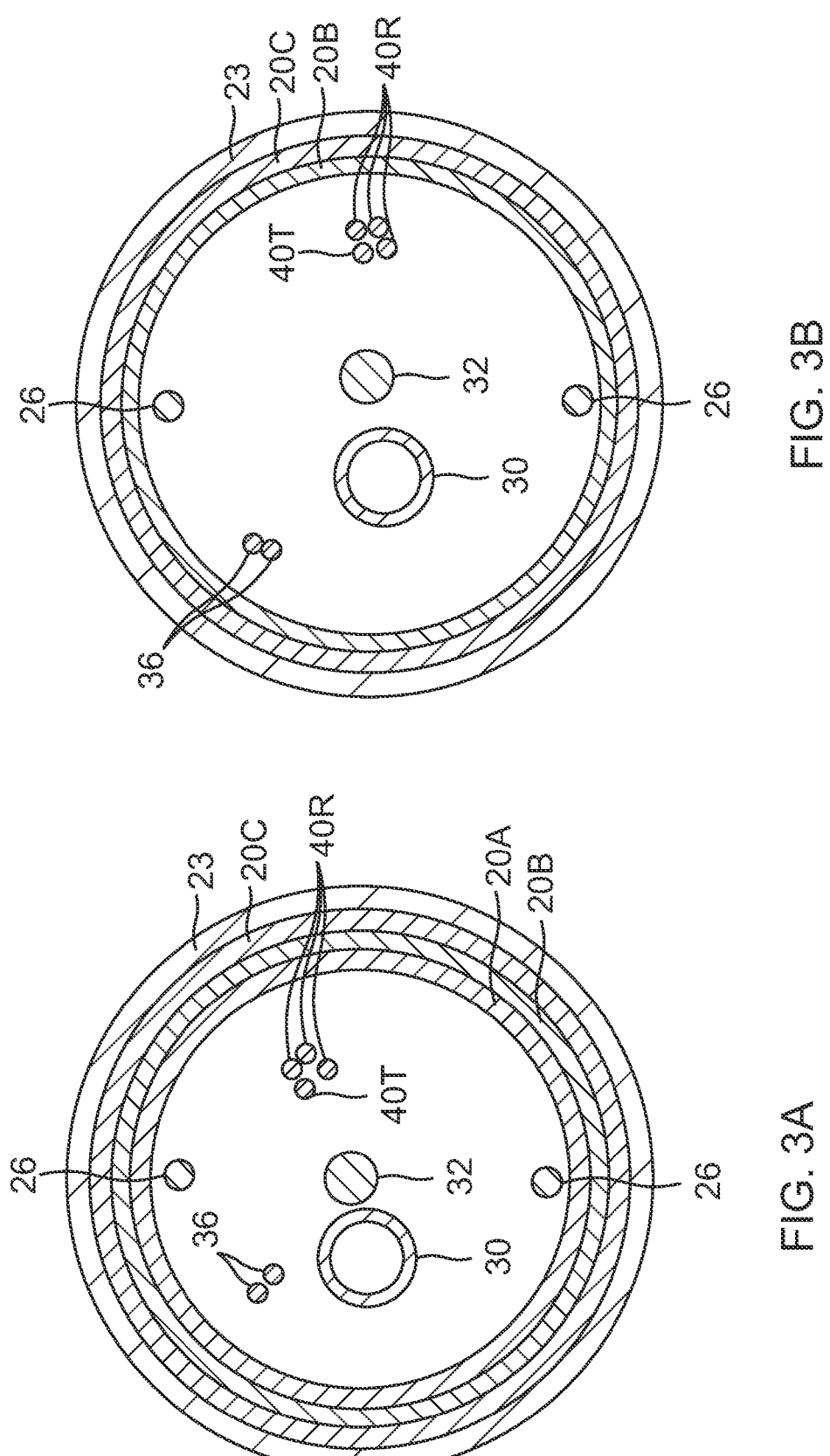
FIG. 3A is an end cross-sectional view of the distal deflection section of FIG. 3, taken along line A-A.
FIG. 3B is an end cross-sectional view of the distal deflection section of FIG. 3, taken along line B-B.

As shown in FIGS. 2B and 3, components extending through the lumen 25 of the stiffener member 24 may include puller wires 26 for bidirectional deflection, lead wire 38 for the distal tip electrode 15, thermocouple wire pair 36, irrigation tubing 30 for delivering irrigation fluid to the distal tip electrode 15, cable 32 for an electromagnetic (EM) force and location sensor subassembly 41 housed in the distal section 14, and lead wires 40T for tip electrode 15 and 40R ring electrodes 17 of the distal section 14. It is understood that the catheter 10 may include a distal electrode section of any configuration, including, for example, focal tip electrodes, lasso electrode assemblies, balloon or basket shaped electrode assemblies, wherein the electrodes may be used for diagnostic and/or therapeutic purposes, such as mapping and/or ablation.

The useful length of the catheter shaft 12, i.e., that portion that can be inserted into the body, can vary as desired. Preferably the useful length ranges from about 100 cm to about 120 cm. The length of the stiffener member is less, so that the catheter shaft 12 has about 5-15 cm of length distally without the stiffener member inside.

With reference to FIG. 3, the distal section 14 includes a short barrier sleeve 46, the distal tip electrode 15 and the pressure sensing subassembly 41 therebetween. The distal tip electrode 15 is configured with a plurality of irrigation ports 48 which weep out fluid delivered by the irrigation tubing 30 (see FIG. 2B), whose distal end terminates in a chamber in the tip electrode. The pressure sensing subassembly 41 includes a resilient member 50 which elastically deforms in response to a force acting on the tip electrode 15, an internal field generator 42 and three electromagnetic sensing coils S1, S2, S3 responsive to the internal field generator 42 which detect deformation of the resilient member 50 in determining the force acting on the tip electrode 15. In the illustrated embodiment, the resilient spring member 50 is a tubular member 51 made of an elastically deformable material, e.g., nitinol. The tubular member 51 has a distal portion 51D, a proximal portion 51P and a mid-portion with a helical slit 52 forming the resilient member 50 which allows longitudinal displacement and angular deflection of the tip electrode 15. Housed in a center lumen of the proximal portion 51P are the electromagnetic sensing coils S1, S2 and S3. The barrier sleeve 46 extends the length of the tubular member, between a distal end of the catheter shaft 12 and the tip electrode 15, to provide a fluid tight seal around the tubular member 51. The barrier sleeve may be constructed of any suitable biocompatible material that is flexible and insulating, including CELCON, TEFLON or heat-resistant polyurethane.

Figures 3C, 3D:
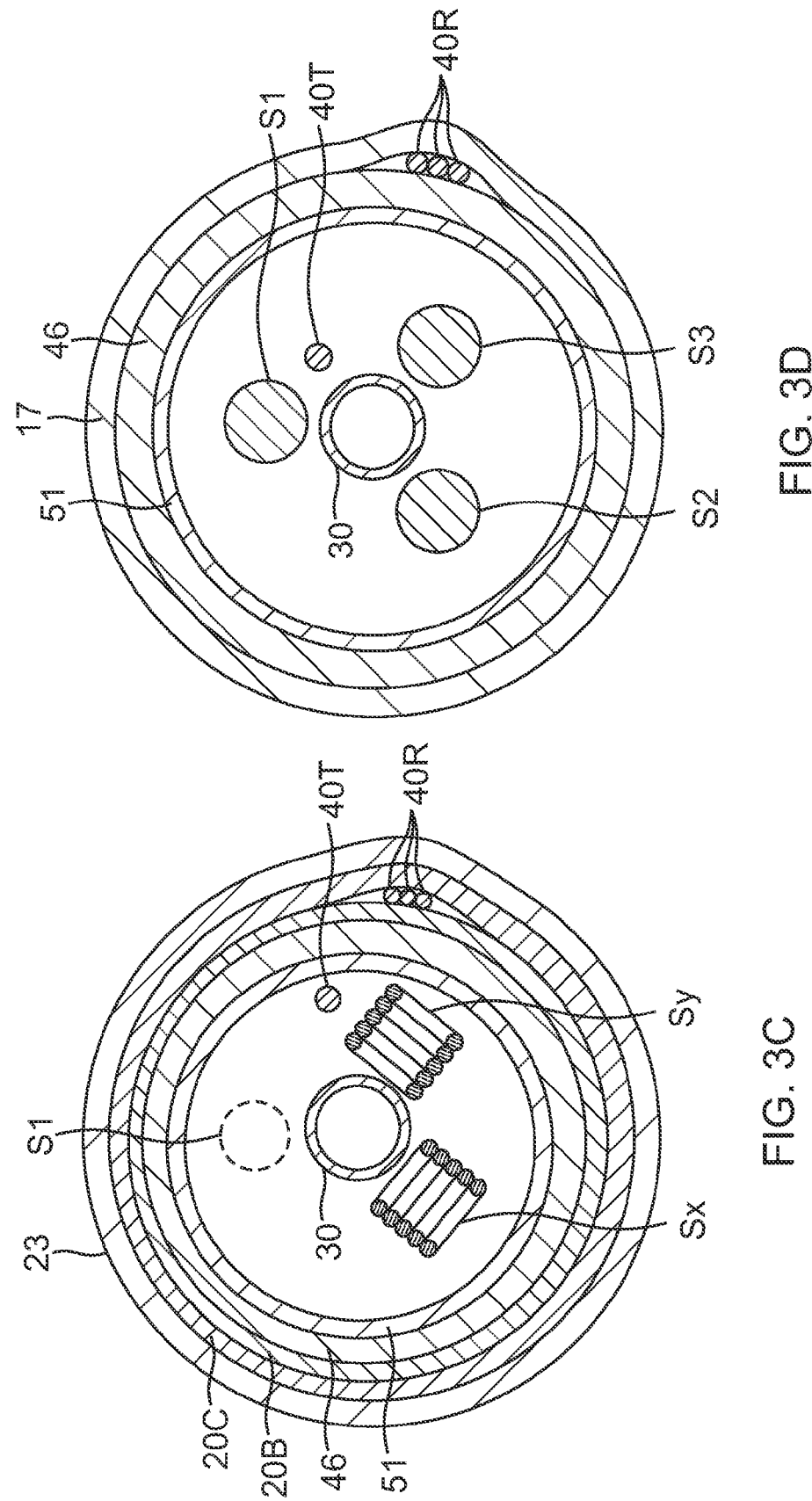
FIG. 3C is an end cross-sectional view of the distal deflection section of FIG. 3, taken along line C-C.
FIG. 3D is an end cross-sectional view of the distal deflection section of FIG. 3, taken along line D-D.

Each of the coils S1, S2 and S3 is generally parallel with the Z or longitudinal axis 53 of the catheter. They are each located at a common longitudinal section in the tubular member 51, but each at different azimuthal angle about the longitudinal axis 53. The coils S1, S2, and S3 are spaced azimuthally 120 degrees apart, at the same radial distance from the longitudinal axis 53. (see FIG. 3D). Longitudinal displacement and/or angular deflection of the distal portion 51D relative to the proximal portion 51P give rise to a differential change in the signal outputs by the coils S1, S2, and S3, depending on the direction and magnitude of deflection, since one or two of these coils move relatively closer to the internal field generator 42. Compressive displacement of the distal portion 51D gives rise to an increase in the signals from each of coils S1, S2, and S3.

Also housed in the proximal portion 51D, sensors Sx and Sy are responsive to external field generators (not shown) which generate magnetic fields in the vicinity of the patient's body (for example, below the patient's bed) to define an external frame of reference, as shown in the art. The coils Sx and Sy are arranged with generally mutually orthogonal axes with each other and with at least one coil, for example, S1 (see FIG. 3C). Accordingly, the coil Sx is aligned with an X axis and the coil Sy is aligned with a Y axis, and both coils are orthogonal to the coil Si which is aligned with the Z axis (longitudinal axis 53) with in an (X, Y, Z) coordinate system.

Electromagnetic or magnetic fields are generated by the external field generators Fx, Fy, and Fz (not shown) and sensed by the sensor coils Sx, Sy, and Sz for detecting position of the catheter. The magnetic fields created by the field generators Fx, Fy, and Fz cause the coils Sx, Sy, and Si to generate electrical signals, with amplitudes that are indicative of the position of the distal section 51D relative to the fixed frame of reference of field generators Fx, Fy, and Fz. In some embodiments, the three field generators Fx, Fy, and Fz generate a magnetic field composed of three differently oriented field components. Each of these field components is sensed by each sensor coil Sx, Sy, and Si, each of which produces a signal composed of three components.

A proximal end of the barrier sleeve 46 and of the proximal portion 51P of the tubular member 51 are received in the welded tubular end portion 21 of the multi-layered coil member 20. Fixedly attached to an inner radial surface of the distal end tubular section 21 is a distal end of each puller wire 26. Accordingly, the distal ends of the puller wires are anchored at or near the distal of the catheter shaft 12, for example, by welds W.

Components including the lead wires 40T and 40R, thermocouple wire pair 36, the irrigation tubing 30 and the sensor cable 32 extend through the welded tubular end portion 21 and into the pressure sensing subassembly 41. The sensor cable 32 includes leads (not shown) to each of the sensors S1, S2, S3, Sx and Sy.

To actuate the puller wires 26, a user manipulates a deflection rocker arm 54 on the control handle 16, as shown in FIG. 1. As known in the art, the rocker arm 54 draws on one or the other puller wire 26 depending on the direction of rotation which deflects the distal section 12D of the catheter shaft in that direction. In accordance with a feature of the present invention, the type or degree of deflection curvature of the catheter 10 as set by a longitudinal position of the stiffener member 24 relative to the catheter shaft 12, and in particular the multi-layer coil member 20, is adjustable by an operator via the deflection curvature adjustment handle 18.

Figure 4:
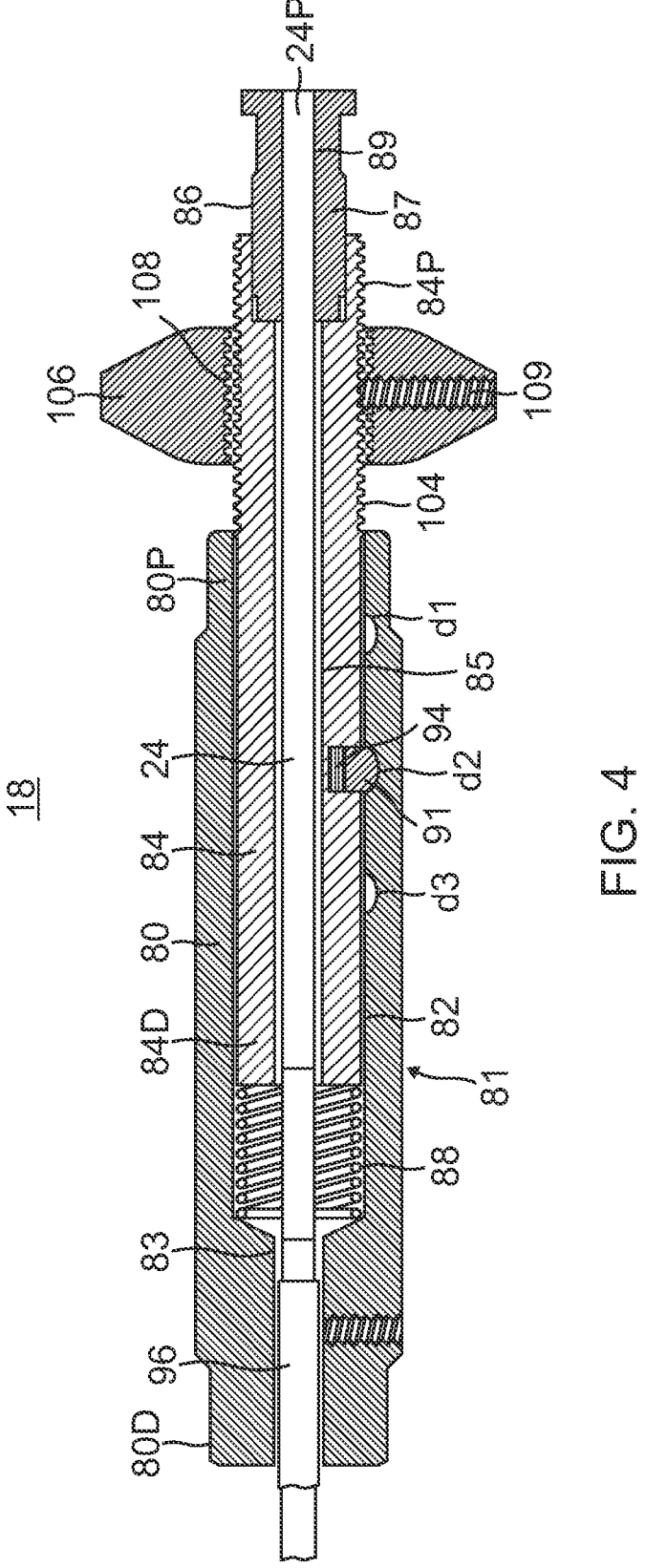
FIG. 4 is a side cross-sectional view of a deflection curvature adjustment handle of FIG. 1.

In the illustrated embodiment of FIG. 4, the deflection curvature adjustment handle 18 comprises a generally cylindrical outer body 80 housing a piston assembly 81. The body 80 has proximal end 80P and distal end 80D. The piston assembly 81 includes a piston 84, a longitudinal piston chamber 82 extending partially therethrough, and a stiffener passage 83 extending partially therethrough. The piston chamber 82 extends from the proximal end 80P of the outer body 80 partway into the handle 18 but does not extend out the distal end 80D of the outer body. The stiffener passage 83, which has a diameter less than that of the piston chamber 82, extends from the distal end of the piston chamber to the distal end 80D of the outer body 80.

The piston 84, having proximal end 84P and distal end 84D, is slidably mounted within the piston chamber 82. A proximal fitting 86 is mounted in and fixedly attached to the proximal end 84P of the piston 84. The proximal fitting 86 includes a tubular distal region 87 that extends distally from the main body of the proximal fitting and into the proximal end 84P of the piston. The piston 84 has a longitudinal axial passage 85 which is coaxial and connects with an axial passage 89 formed in the proximal fitting 86. The stiffener member 24 has a proximal end 24P that is fixed, e.g., by adhesive, to the proximal fitting 86 and thus coupled to the piston so that movement of the piston results in movement of the stiffener member 24. The stiffener member 24 extends through the axial passages 85 and 89 and out the distal end of the deflection curvature adjustment handle 18.

Figures 5A, 5B, 5C:
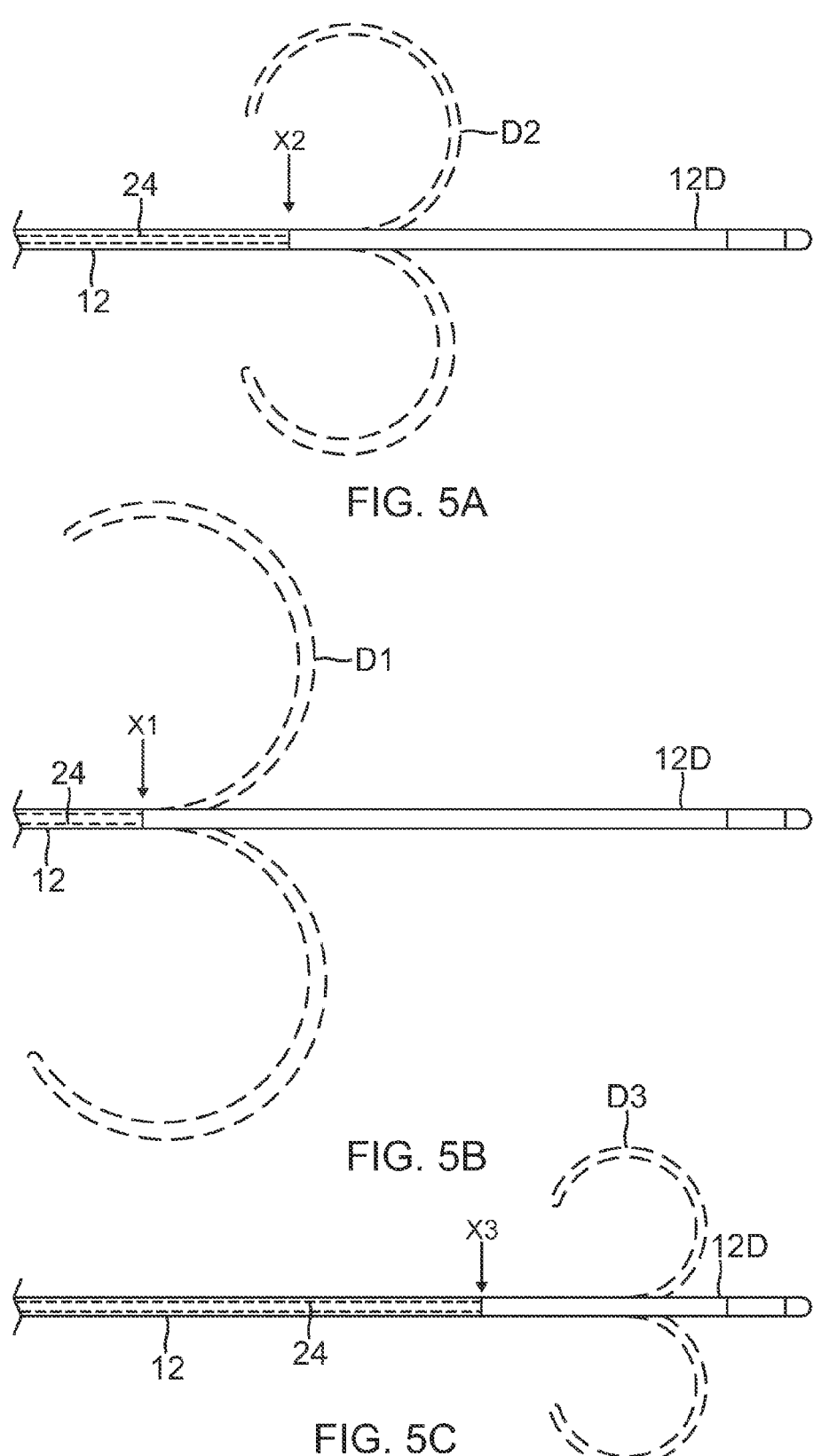
FIGS. 5A, 5B and 5C are schematic representations of symmetrical bi-directional deflection curvatures of different types or tightness provided by the catheter shaft of FIG. 1.

To guide an operator in selecting predetermined types or degrees of deflection curvature of the catheter, the adjustment handle 18 is configured for longitudinal movement of the piston 84 relative to the cylindrical body 80 in a measured or discrete manner. In the illustrated embodiment of FIG. 4, a plurality of recessed detents d1, d2 and d3 are formed on a longitude along an inner radial surface of the piston chamber 82, where each detent is configured to receive and engage with a raised formation, for example, a ridge or, as illustrated, a ball plunger 91 supported and biased by a spring 94 situated in a recess 92, formed on an outer radial surface of the piston 84. Each detent positions the stiffener member 24 within and relative to the catheter shaft 12 such that the distal end of the stiffener member 24 generally sets a location Xi representing a proximal end of the distal deflection section 12D at which its deflection curvature begins. As illustrated in FIGS. 5A, 5B and 5C, locations X1, X2, and X3 enable the distal deflection section 12D to achieve deflection curvatures D1, D2, and D3, respectively. It is understood that the FIGURES, including those illustrating the detents $d_i$ and corresponding locations $X_i$, are not necessarily to scale in relation to each other. It is also understood that the detents may be formed in the outer radial surface of the piston 84, with the raised formation emerging from the inner radial wall of the piston chamber 82.

Optionally, a compression spring 88 may be mounted within the piston chamber 82 to bias movement of the piston relative to the cylindrical body 80 and/or to smooth out this relative movement. The spring 88 may be positioned between the distal end 84D of the distal end 84D of the piston 84 and the distal end of the piston chamber 82. The compression spring 88 can either be arranged between the piston 84 and outer body 80, or can have one end in contact with or fixed to the piston 84, while the other end is in contact with or fixed to the distal end 80D of the outer body 80.

The proximal end of the piston 84 has a threaded outer surface 104. A circular thumb control 106 is rotatably mounted on the threaded outer surface 104 at proximal end of the piston 84. The thumb control 106 has a threaded inner surface 108 that interacts with the threaded outer surface 104 of the piston 84 so that the longitudinal position of the thumb control 106 relative to the proximal end 80P of the outer body 80 is adjustable. The thumb control 106 acts as a stop, limiting the maximum distance that the piston 84 can be pushed distally into the piston chamber 82, and thus the distance that the stiffener member 24 can be extended distally longitudinally relative to the catheter shaft 12. A securing means, such as a tension screw 109 is provided in the thumb control 106 to control the tension between thumb control and piston 84 for locking and releasing the thumb control in a longitudinal position on the proximal end 84P of the piston. As would be recognized by one skilled in the art, the thumb control 106 can be replaced by any other mechanism that can act as a stop, such as a step on the inner surface 82, for limiting the distance that the piston 84 extends into the piston chamber 82, and it is not necessary, although it is preferred, that the stop be adjustable relative to the piston.

From the deflection curvature adjustment handle 18, the stiffener member 24 extends distally through a protective shaft 96 extending between the distal end of the deflection curvature adjustment handle 18 and proximal end of the deflection rocker handle 16. The stiffener member 24 extends through the deflection rocker handle 16 and into the proximal end of the catheter shaft 12.

Figure 6:
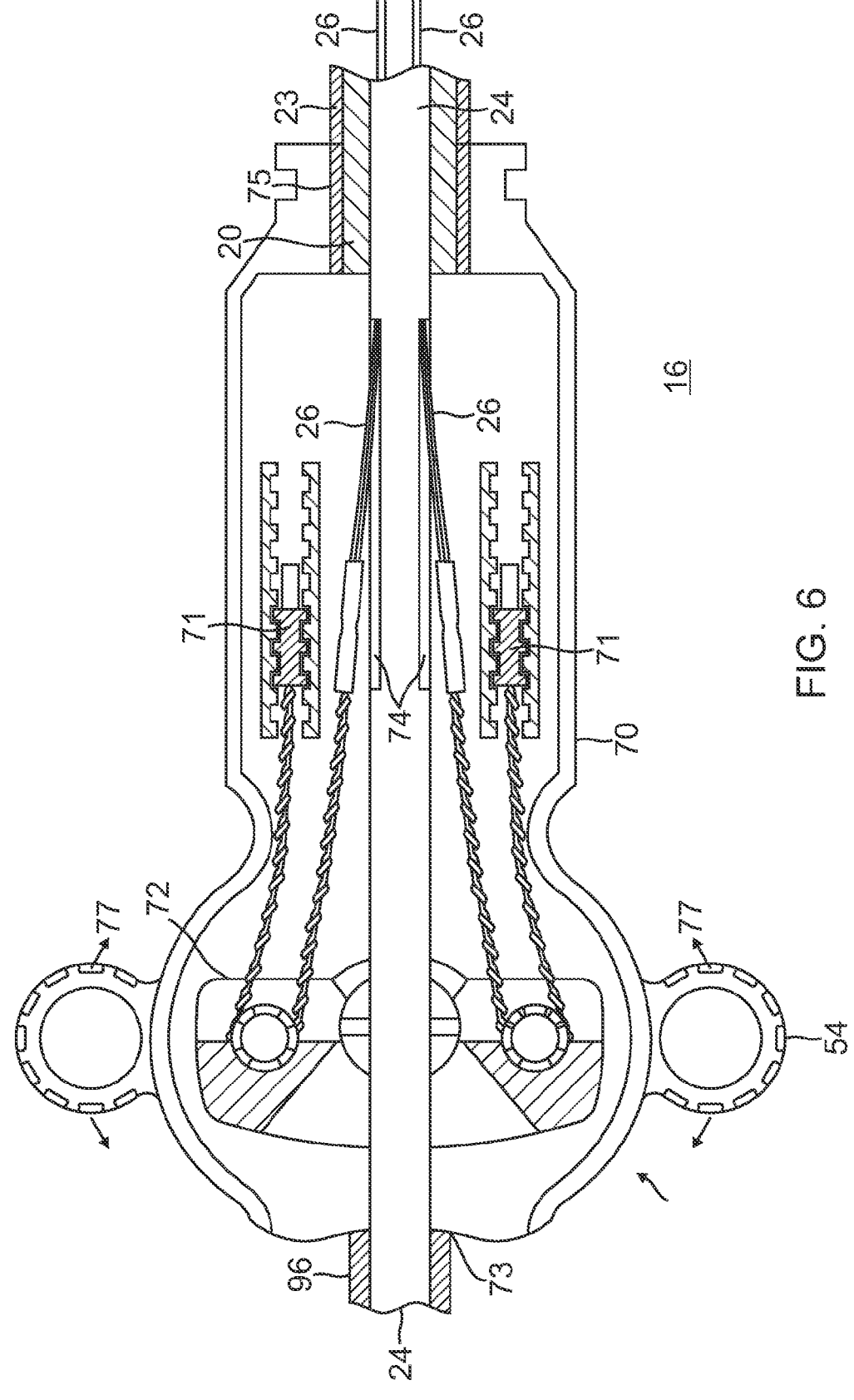
FIG. 6 is a top plan view of a deflection control handle of FIG. 1, with parts broken away.

As shown in FIG. 6, the deflection rocker handle 16 has a housing 70 and pulley assembly 72 around which the puller wires 26 are wrapped to redirect their proximal ends into stops 71 that anchor the proximal ends in the rocker handle 16 at locations distal of the pulley assembly 72. Each of the puller wires 26 may be a subassembly that includes a proximal rope or woven tensile portion that is crimped to the puller wire and wound around the pulley assembly 72. As understood by one of ordinary skill in the art, as an operator pivots or "rocks" the puller assembly 72 in one direction via the rocker arm 54 (sees arrows 77), the puller assembly draws proximally on the one puller wire on that side for deflection in that direction while releasing the other wire distally to facilitate the deflection. The stiffener member 24 extends through the length of the housing 70 between a proximal opening 73 and a distal opening 75, and in between the puller wires 26. In the illustrated embodiment, longitudinal openings or slots 74 are formed in the side wall of the stiffener member 24 so that the puller wires 26 can enter the lumen 25 of the stiffener member 24. The slots 74 have a length sufficient to allow the puller wires 26 to enter the lumen 25 with interfering with the longitudinal movement of the stiffener member 24 relative to the catheter shaft 12. It is understood that the deflection rocker handle 16 and the deflection curvature adjustment handle 18 may be integrated, for example, with the aforementioned piston assembly of the handle 18 may incorporated into the deflection rocker handle 16 distally of the rocker arm 54. Suitable deflection control handles are disclosed in U.S. Pat. Nos. 8,617,087 and 8,747,351, the entire disclosures of which are incorporated herein by reference.

In use, an operator either pulls or pushes piston 84 of the adjustment handle 18 to cause longitudinal movement of the piston relative to the outer body 80 from one detent to another detent, as selected by the operator. This movement causes the stiffener member 24 to move longitudinally within the catheter shaft 12, thereby allowing the operator to vary or adjust the distal end of the stiffener member and thus the type of deflection curvature of the distal deflection section 12D when deflected by the operator via the deflection rocker arm 54 on the control handle 16, as shown in FIGS. 5A, 5B and 5C. By engaging the plunger 91 with a more distal detent, e.g., detent d1, in the adjustment handle 18, as shown in FIG. 4, the piston 84 is set more distally relative to the cylindrical body 80 which positions the distal end of the stiffener member 24 more distally to provide in a smaller or tighter deflection curvature in the distal section 12D. In contrast, by engaging the plunger 91 with a more proximal detent, e.g., detent d3, in the adjustment handle 18, the piston 84 is set more proximally relative to the cylindrical body 80 which positions the distal end of the stiffener member 24 more proximally to provide a larger or looser deflection curvature in the distal section 12D.

In accordance with a feature of the present invention, the catheter 10 is afforded in-plane deflection. As shown in FIGS. 2A and 2B, portions of the multi-layer coil member 20 are fixed or fused, for example, by welding together sections of multiple adjacent coils at 100, in opposite locations along a first diameter 110 to minimize flexion of the coil member 20 within a first plane defined by the first diameter 110 and the longitudinal axis of the coil member 20 while allowing flexion within a second plane generally perpendicular to the first plane. In the illustrated embodiment, the outer layer 20C has portions fused but it is understood that any one or any combinations of the layers 20A, 20B, and 20C may have portions fused together and/or fused to each other to accomplish biased or in-plane deflection. In that regard, the puller wires 26 lie along a second diameter 112 generally perpendicular to the first diameter 110. In the embodiment of FIGS. 2A and 2B, the coil member 20 is fixed at its outer coil layer 20C at intermittent welded or fused locations 100 along its length and along the diameter 110 or the X axis, which minimizes flexion of the coil member 20 within X/Z plane while allowing flexion within the Y/Z plane. In that regard, the puller wires 26 lie along the Y axis generally perpendicular to the X axis.

In lieu of or in addition to the fused or welded sections 100, wire members 101 (shown in broken lines in FIG. 2A) may be welded or fused to the coil member along their length to limit or provide reduced flexibility of the coil member in one plane.

In the embodiment of FIG. 2A, the stiffener member 24 is formed with an even distal end 24 to provide symmetrical bidirectional deflection, as shown in FIGS. 5A, 5B and 5C. An even distal end sets a common location Xi along the length of the catheter shaft 12 for initiation of the deflection curvature (or a proximal end of the distal deflection section 12D) regardless of which puller wire is drawn for deflection.

Figure 7:
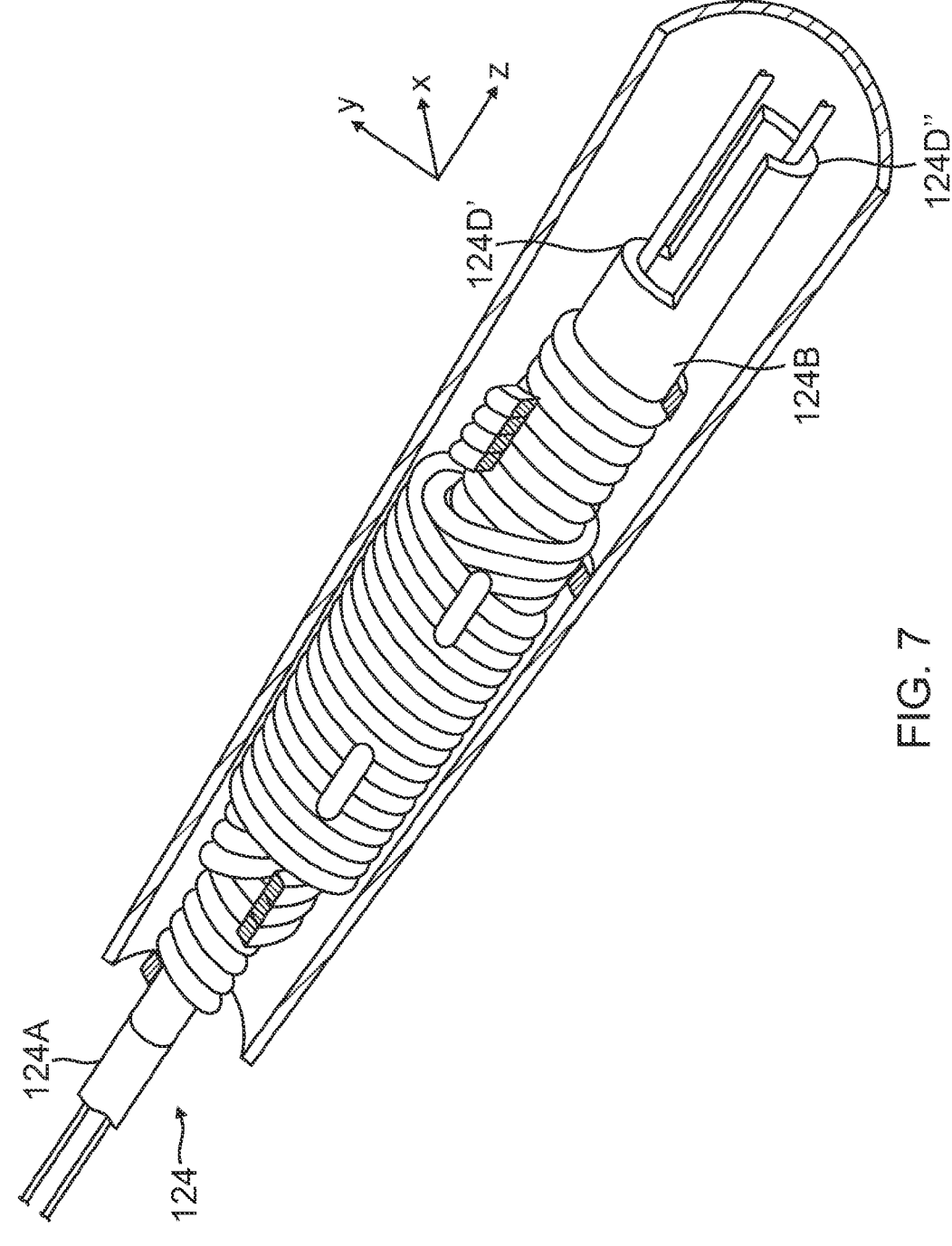
FIG. 7 is a perspective view of a catheter shaft, in accordance with another embodiment of the present invention.
Figures 8A, 8B, 8C:
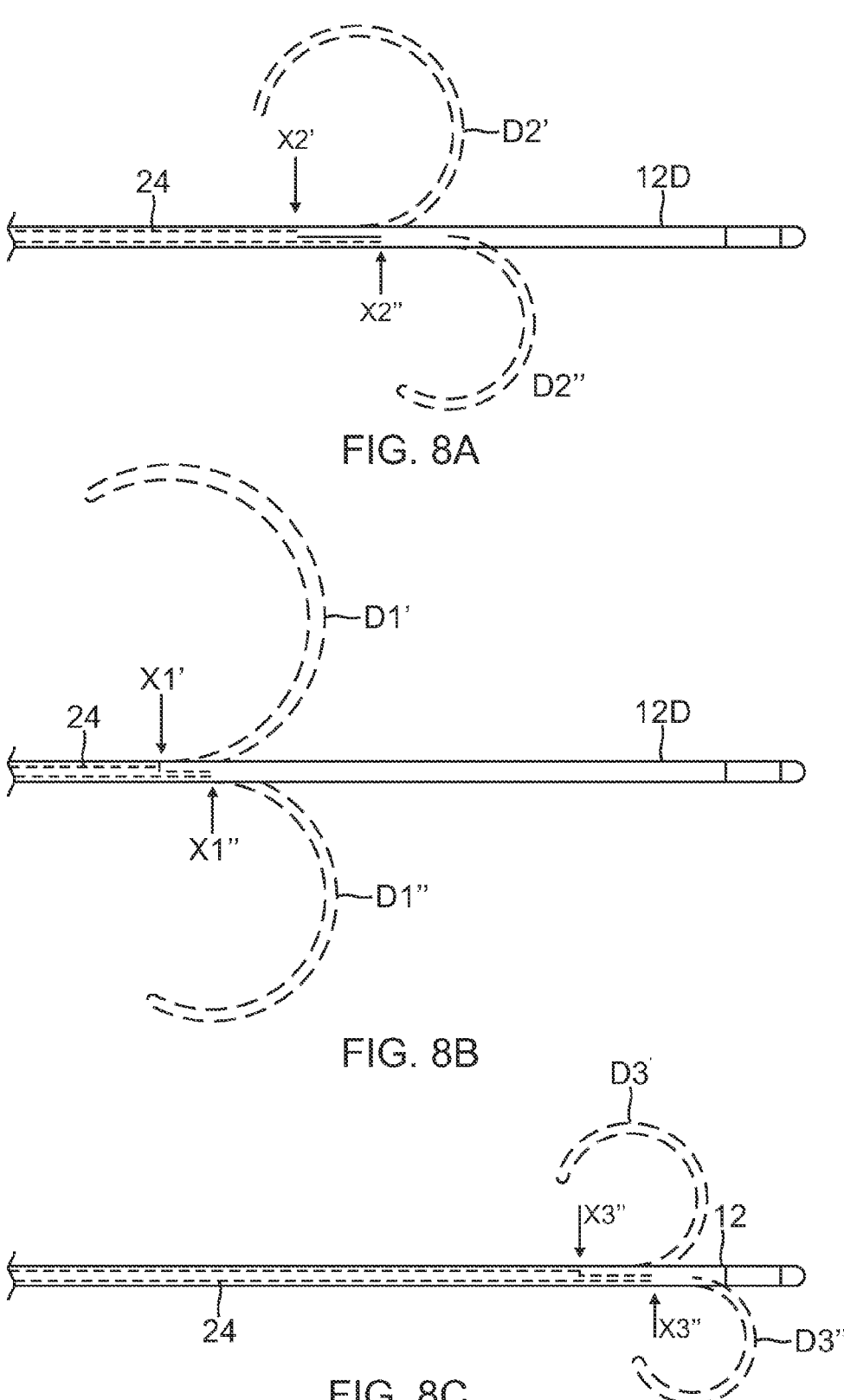
FIGS. 8A, 8B and 8C are schematic representations of asymmetrical bi-directional deflection curvatures of different types or tightness provided by the catheter shaft of FIG. 7.

In accordance with a feature of the present invention, stiffener member 124 in accordance with another embodiment as shown in FIG. 7 is formed with uneven (including, e.g., angled, notched or stepped) distal ends 124D' and 124D" to provide asymmetrical bidirectional deflection, as shown in FIGS. 8A, 8B and 8C. For each longitudinal position of the stiffener member 24 relative to the catheter shaft 12, the distal section 12D has a first deflection curvature D1' with a first deflection initiation location X1' (or a first proximal end of the distal deflection section 12D) for one puller wire corresponding with the distal end 124D', and a second deflection curvature D1" with a second deflection initiation location X1" (or a second proximal end of the distal deflection section 12D) for the other puller wire corresponding with the distal end 124D".

To ensure that the portion of the stiffener member 124 extending to the more distal end 24D" has sufficient rigidity to enable deflection on that side of the stiffener member 124, the stiffener member 124 may have a two part construction comprising sections 124A and 124B, wherein the material(s) of which the section 124B is has sufficient rigidity to support the distal end 124D" against excessive flexing or breakage during deflection. For example, the section 124A is constructed of a plastic material and the section 124B is constructed of nitinol, stainless steel, or other suitable metal.

Figure 9:
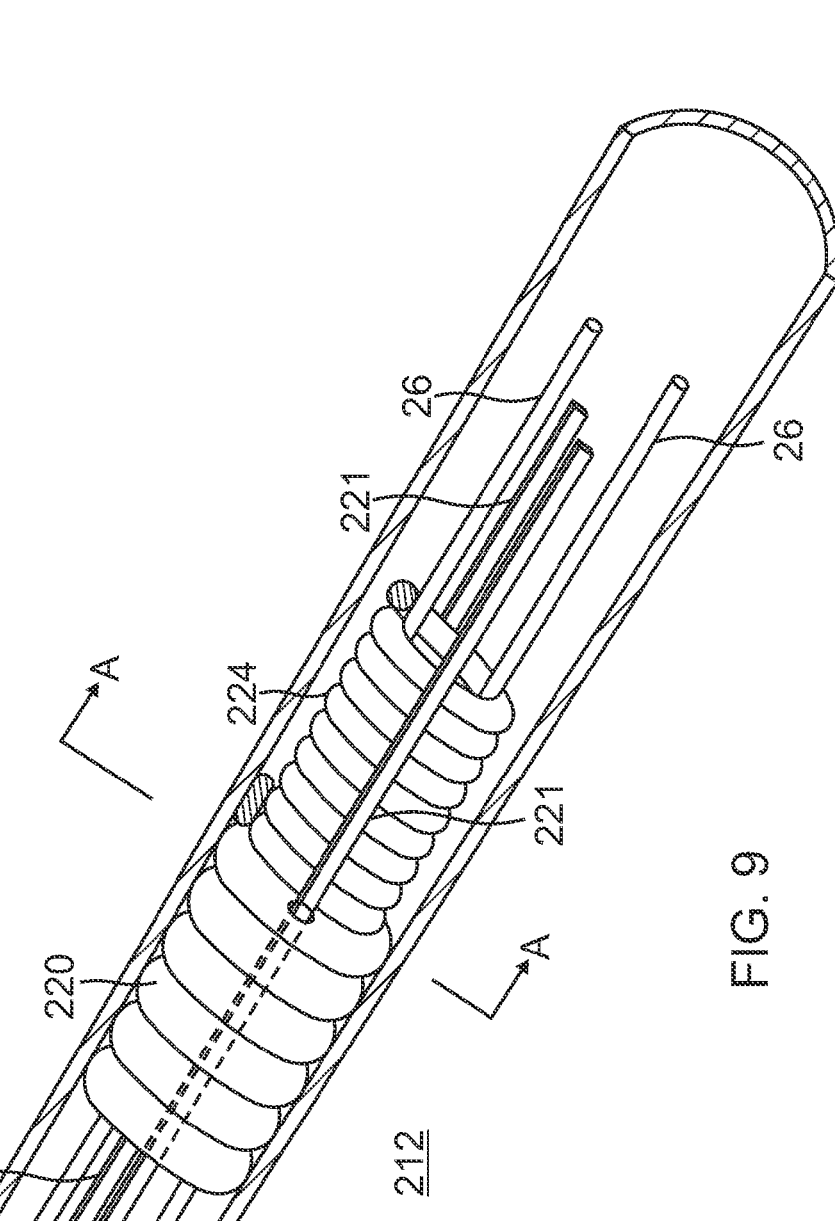
FIG. 9 is a perspective view of a catheter shaft, in accordance with yet another embodiment of the present invention.
Figure 9A:
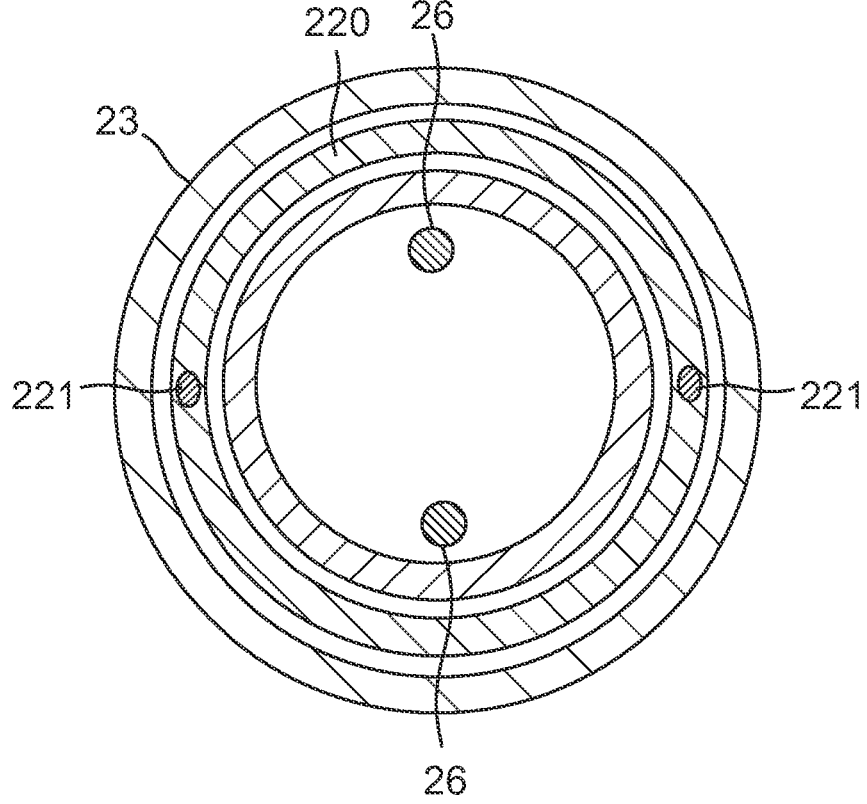
FIG. 9A an end-cross-sectional view of the catheter shaft of FIG. 9, taken along line A-A.

In an alternate embodiment of FIGS. 9 and 9A, a catheter shaft 212 has an outer thin-walled coiled tubular member 220 with a pair of struts 221 embedded or otherwise affixed in opposing locations along a diameter of the tubular member 120. The struts 221 promote bidirectional deflection in a plane generally perpendicular to the diameter. Suitable materials for constructing the struts 221 include, for example, a stiffer polymer or metal wire. Extending through a lumen 122 of the outer coiled tubular member 120, an inner stiffener member 124 has a coiled tubular configuration which minimizes the risk of the stiffener member kinking.

II. Exemplary Guiding Sheath Assembly with Variable Deflection Curvatures

In some procedures, the physician may wish to introduce catheter 10 (see FIG. 1) into the patient via a guiding sheath. In some such procedures, the guiding sheath may be inserted into the patient (e.g., via the leg or groin of the patient); and then be advanced along a vein or artery to reach a position in or near the heart. Once the guiding sheath is suitably positioned in the patient, the physician may then advance end effector 14 and catheter 10 into the guiding sheath until end effector 14 exits the distal end of the guiding sheath. The physician may then operate catheter assembly 10 to provide EP mapping, ablation, or any other kind of operations in or near the heart of the patient. It may be desirable to steer the guiding sheath to facilitate placement of the various catheters 10 in or near the heart. To that end, a guiding sheath assembly may include a guiding shaft assembly that allows the physician to change a deflection curvature near the distal end of the shaft assembly, to assist in further navigating the veins or artery to reach a position in or near the heart.

Figure 10:
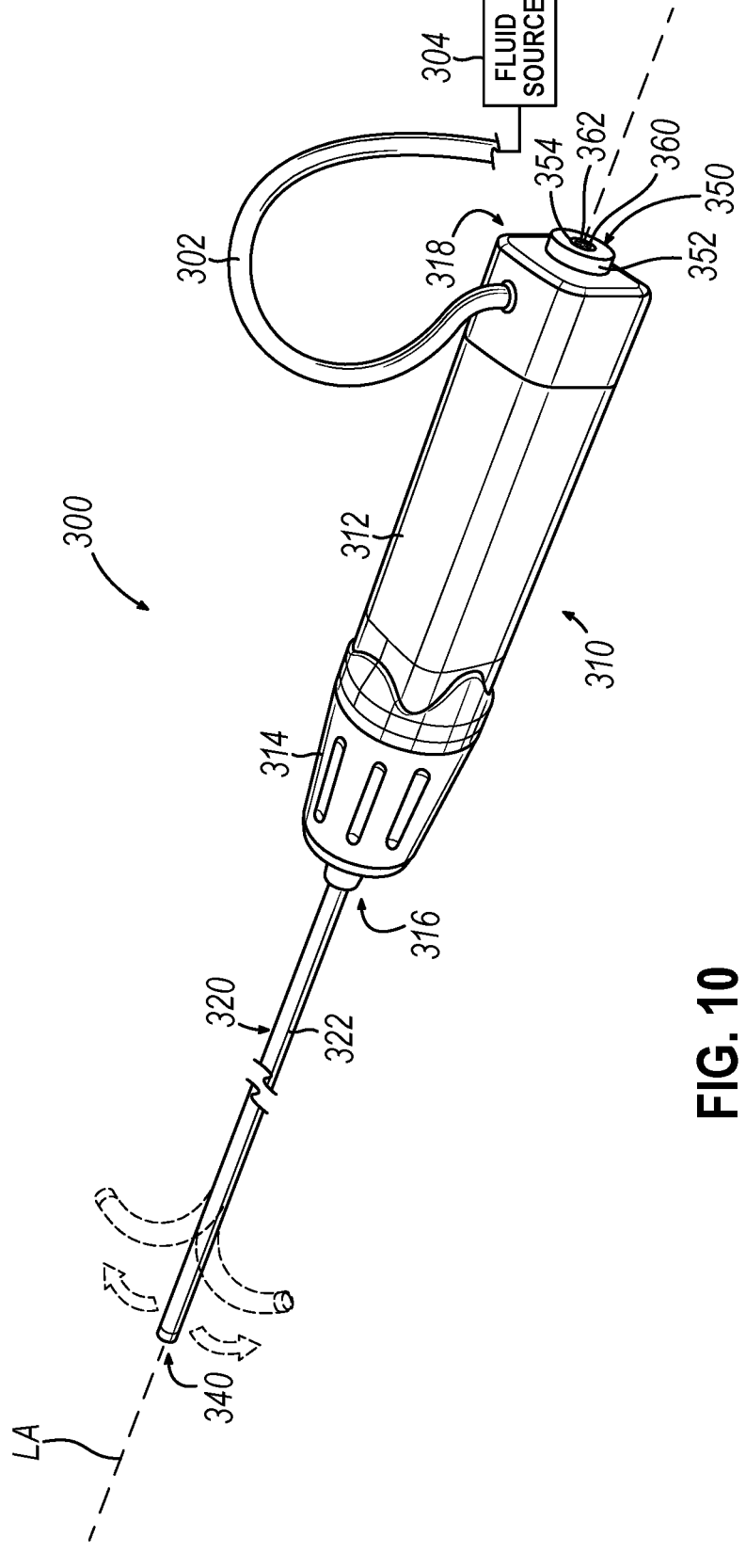
FIG. 10 depicts a perspective view of an exemplary guiding sheath assembly that may be used with the catheter of FIG. 1.

FIG. 10 shows an example of a guiding sheath assembly 300 that may be used in such procedures. Guiding sheath assembly 300 of this example includes a handle assembly 310 and a guiding shaft assembly 320 including a hollow shaft 322 extending distally from a distal end 316 of handle assembly 310. Handle assembly 310 is configured for grasping by a casing 312. The open distal end 340 of the hollow shaft 322 is operable to deflect laterally away from a longitudinal axis LA of the shaft 322. This deflection is controlled by a rotary knob 314 at distal end 316 of handle assembly 310. Rotary knob 314 is rotatable relative to casing 312, about the longitudinal axis LA, to thereby actuate components that drive lateral deflection of open distal end 340 of hollow shaft 322. By way of example only, such actuation components may include one or more pull wires, bands, or various suitable structures as will be apparent to those skilled in the art in view of the teachings herein.

As shown in FIG. 10, a fluid tube 302 extends laterally from the proximal end 318 of handle assembly 310. Fluid tube 302 of this example is in fluid communication with a hollow interior (not shown) defined within handle assembly 310; and the hollow interior is in fluid communication with the interior of hollow shaft 322. Fluid tube 302 of the present example is further in fluid communication with a fluid source 304. By way of example only, fluid source 304 may contain saline or any other suitable fluid. In some instances, fluid from fluid source 304 is communicated through fluid tube 302, a hollow interior region defined within handle assembly 310, and the interior of hollow shaft 322, to thereby flush the fluid path defined by fluid tube 302, the hollow interior region defined within handle assembly 310, and the interior of hollow shaft 322.

As shown in FIG. 10, proximal end 318 of handle assembly 310 further includes an insertion port 350. Insertion port 350 is aligned with the longitudinal axis LA and provides a port for inserting end effector 14 and catheter 10 into hollow shaft 322. Insertion port 350 of this example includes an annular protrusion 352 defining an opening 354. Protrusion 352 protrudes proximally from casing 312 at proximal end 318. In some versions, protrusion 352 is omitted.

A seal 360 is positioned within opening 354. By way of example only, seal 360 may include an elastomeric membrane or other suitable structure as will be apparent to those skilled in the art in view of the teachings herein. Seal 360 of the present example further includes a slit arrangement 362 that is configured to facilitate insertion of an instrument (e.g., catheter 10) or an insert member (not shown) through seal 360. In the present example, slit arrangement 362 is in the form of a "+" sign, though any other suitable kind of configuration may be used. When nothing is inserted through seal 360, seal 360 is configured to provide a fluid-tight seal that prevents fluid from escaping the portion of the above-described fluid path defined within handle assembly 310 via insertion port 350; and prevents air from entering the above-described fluid path defined within handle assembly 310 via insertion port 350. When an instrument is inserted through seal 360, seal 360 still substantially maintains a fluid-tight seal of port 350, preventing fluid from escaping the above-described fluid path defined within handle assembly 310 via insertion port 350; and preventing air from entering above-described fluid path defined within handle assembly 310 via insertion port 350, while still allowing the inserted instrument to translate relative to seal 360. Thus, regardless of whether an instrument is disposed in insertion port 350, seal 360 may prevent fluids from leaking out through insertion port 350 and prevent air from being aspirated into the heart of the patient via insertion port 350.

Figures 11A, 11B, 11C:
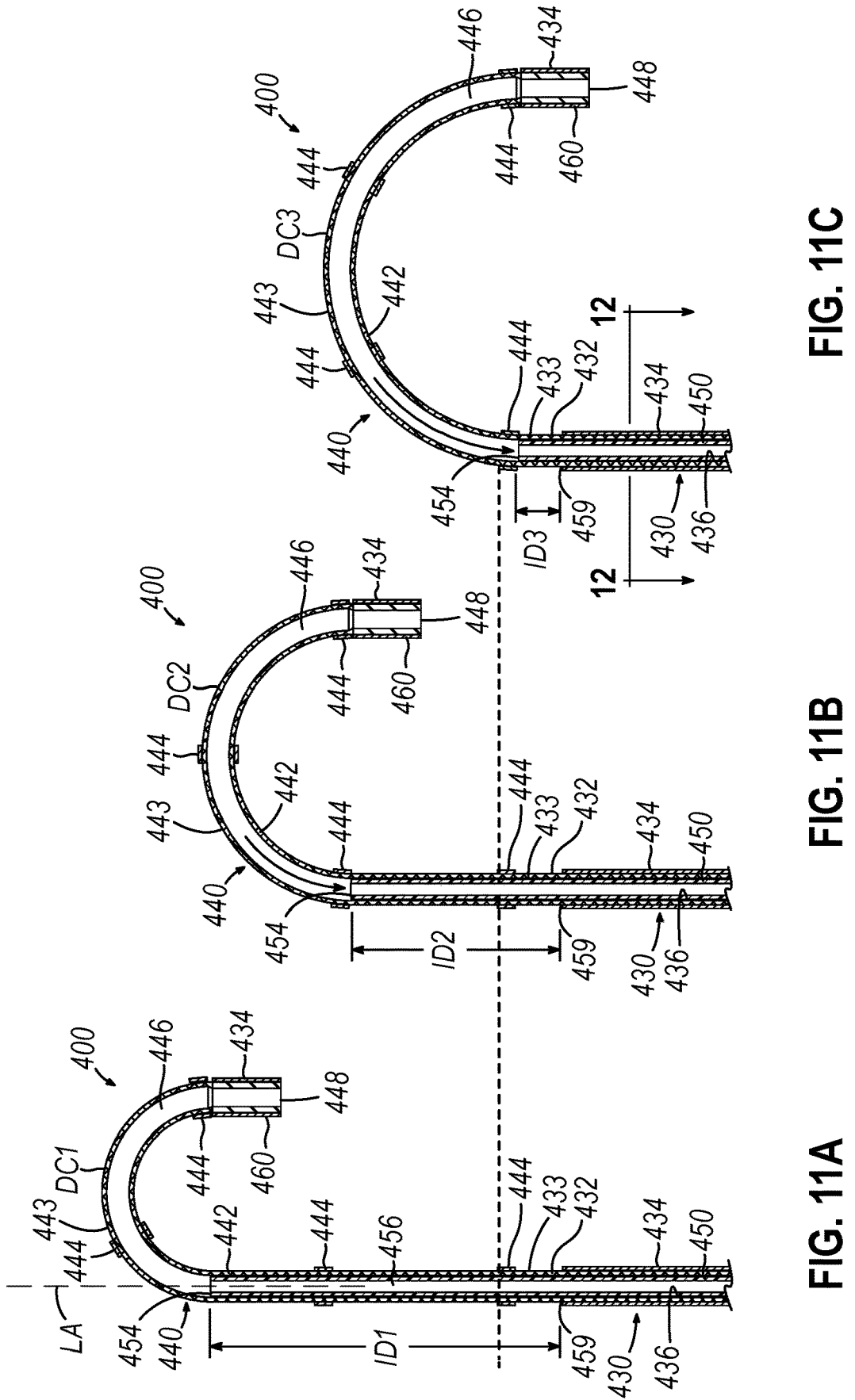
FIGS. 11A, 11B, and 11C are cross-sectional views of an exemplary guiding shaft assembly including a stiffener member in various deflected curvatures for use with the guiding sheath assembly of FIG. 10, with the guiding shaft assembly of FIG. 11A having a tighter deflection curvature relative to the deflection curvature of FIG. 11B; and the deflection curvature of FIG. 11B having a tighter deflection curvature relative to the deflection curvature of FIG. 11C.

A. Exemplary Guiding Shaft Assembly with Variable Stiffener Member Located within a Proximal and Distal Lumen As noted above, it may be desirable to provide a guiding shaft assembly in a guiding sheath assembly that allows the physician to selectively adjust a deflection curvature of the guiding shaft assembly to assist in further navigating the cardiovascular system to reach a position in or near the heart. FIGS. 11A-11C show an example of a guiding shaft assembly 400 that may be incorporated into guiding sheath assembly 300. The guiding shaft assembly 400 of this example includes a proximal section 430, a distal section 440, and a stiffener member 450. The proximal section 430 is an elongate tubular member and extends distally from the handle assembly 310 (see FIG. 10 to the proximal shaft end 459. The proximal section 430 includes a proximal shaft 432 and a lubricious coating 434. The proximal shaft 432 is sized to fit within the patient's vein or artery. The proximal shaft 432 defines a proximal lumen 436 and may be constructed of a plastic or a metal having flexible yet rigid properties such as braided stainless steel or nitinol. The lubricious coating 434 is provided on a proximal shaft exterior wall 433. The lubricious coating 434 may be configured to reduce friction between the proximal section 430 and the patient's vein or artery. The lubricious coating 434 may also be configured to resist a natural lateral bias of the proximal shaft 432. The proximal section 430 defines a proximal lumen 436 configured to receive the catheter 10 (see FIG. 1). The proximal lumen 436 may also be coated with a material that is configured to reduce friction between the catheter 10 and the proximal lumen 436. Various suitable coatings will be apparent to those skilled in the art in view of the teachings herein. Alternatively, such coatings may be omitted.

The distal section 440 extends distally from the proximal shaft end 459 to a distal tip 448. The distal section 440 includes a distal shaft 442, a plurality of bands 444, and distal tip 448. The distal section 440 is laterally biased into a pre-curved shape away from the longitudinal axis LA. The distal tip 448 is hollow and is configured to allow the catheter 10 to pass distally through the distal tip 448. The distal tip 448 may be chamfered or rounded to facilitate navigation through a patient's veins and arteries by a physician without binding or kinking on an inner surface of the patient's veins and arteries. The distal shaft 442 is sized similarly to the proximal shaft 432. The distal shaft 442 may be constructed of the same materials as the proximal shaft 432. In an example when the proximal shaft and distal shaft 432, 442 are constructed from the same materials, the proximal shaft 432 ends where the lubricious coating 434 ends and the distal shaft 442 begins at the proximal shaft end 459. In the case when the proximal shaft and distal shaft 432, 442 are constructed from the same materials, the distal shaft 442 may additionally be treated to facilitate lateral deflection state such as through heat treating. Additional treatments apparent to those skilled in the art may be applied to the distal shaft 442 to give the distal shaft 442 a lateral bias. As another variation, the distal shaft 442 may be constructed of materials that are different from proximal shaft 432. When constructed of dissimilar materials, the proximal shaft end 459 may be operatively connected at the proximal section distal end 449 by welding, brazing, weaving, or otherwise. The distal shaft 442 may be constructed of a shape memory alloy such as nitinol.

The distal shaft 442 defines a distal lumen 446 configured to receive the catheter 10. The distal lumen 446 is sized similarly to the proximal lumen 436 and is configured to allow the catheter 10 to easily transition from the proximal lumen 436 to the distal lumen 446. The distal shaft 442 may also have a lubricious coating 434 configured to aid sliding the distal shaft 442 within the patient's vein or artery. As shown, this lubricious coating 434 may be located on a distal portion 460 of the distal section 440 (e.g., only on distal tip 448) or may be located along any length of the distal shaft exterior wall 443. The coating on the distal portion 460 may resist the lateral bias of the distal section 440 and straighten the distal portion 460. The distal lumen 446 may also have a lubricious coating 434 configured to aid translating the catheter 10 and/or the stiffener member 450 within the distal lumen 446.

The plurality of bands 444 are positioned along the length of the distal shaft 442. The plurality of bands 444 may be constructed of a rigid, surgically safe plastic or metal such as stainless steel. By way of example only, the plurality of bands 444 may include one or more rings, surface effects, or various suitable support structures as will be apparent to those skilled in the art in view of the teachings herein. The plurality of bands 444 are configured to provide support to the distal shaft 442 and may provide tactile feedback to the user as the distal section 440 translates along the patient's vein or artery. This tactile feedback may aid the user in knowing the location of the distal section 440. In some versions, one or more of the bands 444 serves as an electrode. For instance, one or more of bands 444 may be operable to provide EP mapping by picking up potentials from tissue contacting bands.

The plurality of bands 444 shown in the current example are spaced equidistantly from each other along the length of distal shaft 442. A first band 444 is located distal of proximal end of the distal shaft 442, a second band 444 is located distal of the first band 444, a third band 444 is located distal of the second band 444, and a fourth band 444 is located distal of the third band 444 and proximal of the distal tip 448. By way of example only, the bands 444 may be positioned progressively closer to each other approaching the distal tip 448 or progressively closer to each other approaching the proximal shaft end 459. In the current example, there are four bands 444. By way of example only, there may be no bands 444, two bands 444, six bands 444, eight bands 444, or any number of bands 444 may be used to provide the support and tactile feedback. The bands 444 may be located within the distal lumen 446. In an example with the bands 444 within in the distal lumen 446 the bands 444 are configured to provide support to the distal section 440 and provide the user tactile feedback of the stiffener member 450 location.

The stiffener member 450 is constructed of a rigid yet flexible material such as metal or plastic. One such exemplary material is polytetrafluorethylene (PTFE). The stiffener member 450 is sized to fit within both the proximal and distal lumens 436, 446. The stiffener member 450 defines a member lumen 456 that is sized to slidably accept the catheter 10. The stiffener member 450 has stiffer properties (e.g., lateral rigidity) relative to the distal shaft 442. The stiffener member 450 is configured to selectively translate distally within the proximal and distal lumens 436, 446. The stiffener member 450 is configured to counter the lateral bias of the distal shaft 442. The stiffener member 450 counters the lateral bias of the distal shaft 442 and thereby provides a variable deflection curvature DCx (i.e., radius of curvature) in distal shaft 442, with the deflection curvature $DC_x$ being based on the longitudinal position of stiffener member 450 in distal shaft 442. The portion of the distal shaft 442 that is distally positioned relative to stiffener member end 454 retains its laterally bias deflection and results in a tighter deflection curvature DCx relative to the portion of the distal shaft 442 that is between the stiffener member end 454 and the proximal shaft end 459 that is rendered relatively straight. The deflection curvature DCx width is the transverse distance from the longitudinal axis LA to the centerline axis of the distal tip 448; and is used as a reference for identifying changes between the various deflection curvatures DCx.

While distal shaft 442 is resiliently biased to provide a 180-degree retrograde deflection angle in this example, such that the centerline axis of distal tip 448 is parallel with the longitudinal axis LA, other variations of distal shaft 442 may have a resilient bias that provides an oblique deflection angle, such that the centerline axis of distal tip 448 is obliquely oriented relative to the longitudinal axis LA.

In order to control the deflection curvature DCx in the present example, the stiffener member 450 may be manually inserted distally through the insertion port 350 (FIG. 10), further through the proximal lumen, and yet further through the distal lumen 446. As another merely illustrative example, stiffener member 450 may be integrated into guiding shaft assembly 320; with a movable actuator (e.g., slider, etc.) on handle assembly 310 that is operable to selectively translate stiffener member 450 within distal lumen 446. In either case, the stiffener member 450 is inserted to an insertion depth IDx. The insertion depth IDx is the distance from a proximal shaft end 459 to the stiffener member end 454. The insertion depth IDx has an inverse relationship to the deflection curvature DCx width. A relatively longer insertion depth IDx results in a relatively smaller deflection curvature DCx width.

FIG. 11A shows the stiffener member 450 inserted to an insertion depth ID1. FIG. 11B shows the stiffener member 450 inserted to an insertion depth ID2. FIG. 11C shows the stiffener member 450 inserted to the insertion depth ID3. The insertion depth ID1 is relatively longer than the insertion depth ID2 that is shown in FIG. 11B. The insertion depth ID2 is relatively shorter than the insertion depth ID1 but longer than an insertion depth ID3. The insertion depth ID3 is relatively shorter than the insertion depth ID2.

Accordingly, the deflection curvature DC1 is relatively tighter than the deflection curvature DC2 that is shown in FIG. 11B; the deflection curvature DC2 is looser than the deflection curvature DC1 and tighter than the deflection curvature DC3; and the deflection curvature DC3 is relatively looser than the deflection curvature DC2. By way of example only, the deflection curvature DC1 width may be approximately 20 mm; the deflection curvature DC2 width may be approximately 32 mm; and the deflection curvature DC3 width may be approximately 55 mm. Alternatively, any other suitable deflection curvatures DCx may be provided.

It should also be understood that any suitable number of different deflection curvatures DCx may be achieved by further varying the insertion depth IDx of stiffener member 450. An infinite range or a finite number of the deflection curvatures DCx may be created. Three insertion depths IDx and corresponding deflection curvatures DCx are shown and described herein only as illustrative examples. By way of further example only, the deflection curvature DCx widths may vary within a range from approximately 0 mm to approximately 75 mm. In some examples, the deflection curvature DCx width may vary within a range from approximately 0 mm to approximately 75 mm; and more specifically from approximately 20 mm to approximately 55 mm.

Figure 12:
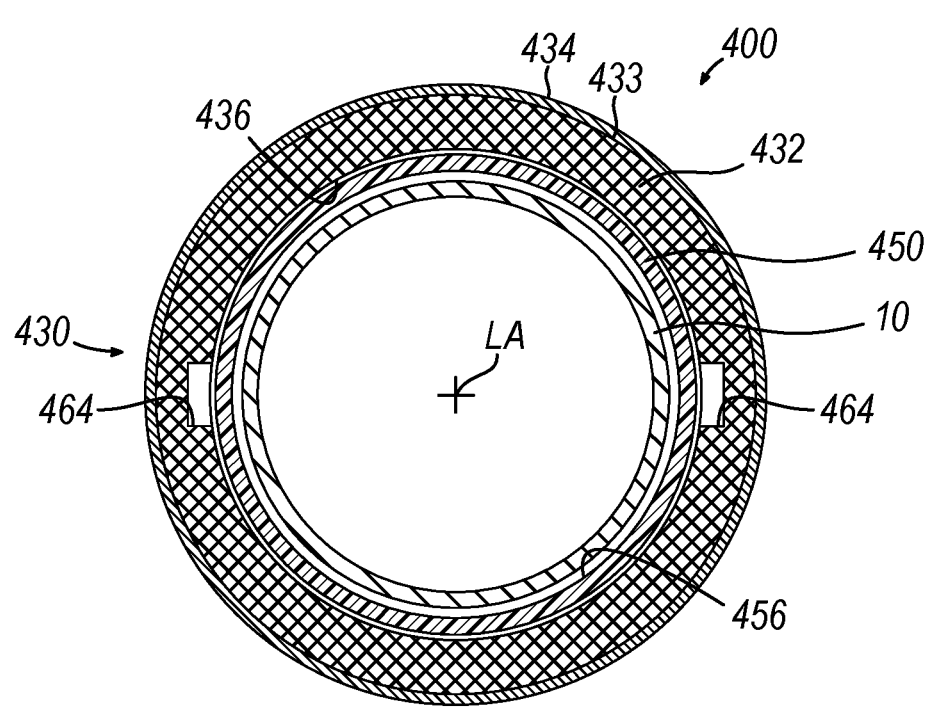
FIG. 12 shows an end-cross-sectional view of the guiding shaft assembly of FIG. 11C, taken along line 12-12 of FIG. 11C.

FIG. 12 shows the guiding shaft assembly 400 of 11C taken along line 12-12. The lubricious coating 434 is shown on the proximal exterior shaft wall 433 of the proximal shaft 432. The stiffener member 450 is disposed within the proximal lumen 436. The catheter 10 is disposed within the member lumen 456. The proximal and distal shaft 432, 442 may further include at least one side lumen 464 configured to accept at least one pull wire, stiffener member, or some other element. The at least one side lumen 464 may communicate with the proximal and distal lumens 436, 446 as shown. The at least one side lumen 464 may be defined by the proximal and distal shaft 432, 442 in a hollow region that extends distally parallel to the longitudinal axis within the proximal lumen 436 and the proximal exterior shaft wall 433. In other examples, the guide shaft assembly (400) may include be at least one pull wire. By way of example only, the proximal and distal shaft 432, 442 may include four, six, or eight pull wires within four, six, or eight respective side lumens 464. The at least one side lumen 464 and the at least one pull wires may be located radially around the proximal and distal lumens 436, 446. Examples of pull wires are described in greater detail below. In some versions of guiding shaft assembly 400, side lumens 464 are simply omitted, such that guiding shaft assembly 400 lacks side lumens 464.

B. Exemplary Guiding Shaft Assembly with Variable Stiffener Member within a Side Lumen As noted above, it may be desirable to provide a guiding shaft assembly in a guiding sheath assembly that allows the physician to selectively adjust a deflection curvature of the guiding shaft assembly to assist in further navigating the cardiovascular system to reach a position in or near the heart. It may be further desirable to provide a guiding shaft assembly that includes all such functionality while minimizing the amount of space taken up within the proximal and distal lumens, thereby further facilitating introduction of a catheter through such proximal and distal lumens.

Figure 13:
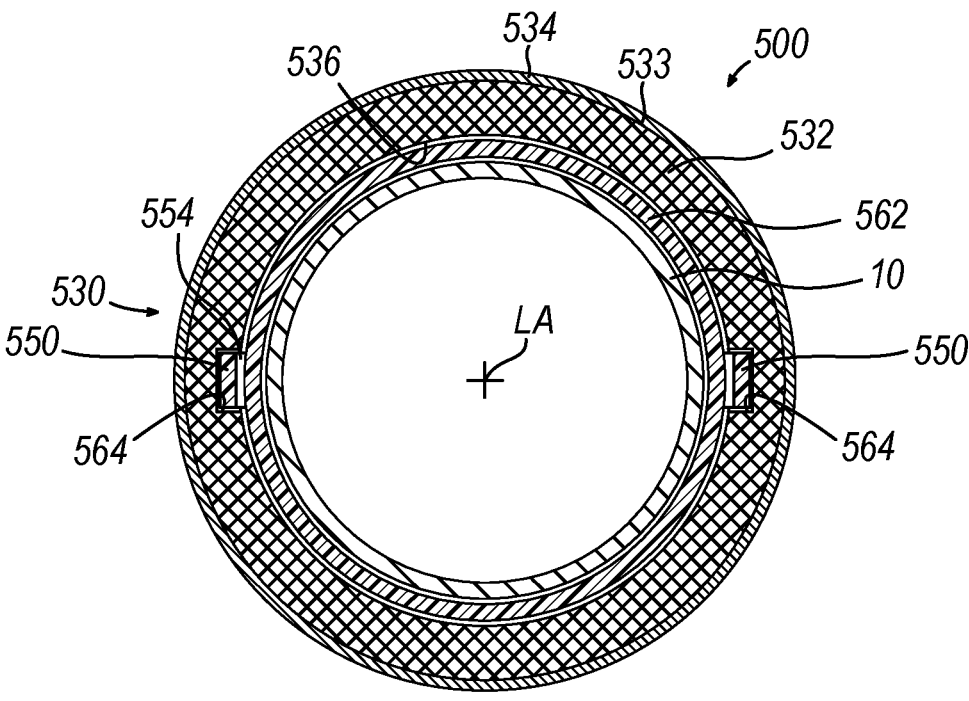
FIG. 13 shows an end-cross-sectional view of an exemplary variation of the guiding shaft assembly of FIG. 11C, taken along line 12-12 of FIG. 11C, including a stiffener member within a side lumen.

FIG. 13 shows another example of a guiding shaft assembly 500 similar to the guiding shaft assembly 400. The view of guiding shaft assembly 500 in FIG. 13 is similar to the view of guiding shaft assembly 400 in FIG. 12. The guiding shaft assembly 500 of this example has a proximal section 530 that is different from proximal section 430; and a distal section (not shown) that similar to the distal section 440. The proximal section 530 includes a proximal shaft 532. The distal section of guiding shaft assembly 500 has a distal shaft that is similar to distal shaft 442 of guiding shaft assembly 400. The proximal shaft 532 and distal shaft define a proximal lumen 536 and a distal lumen (now shown), respectively. The proximal shaft may include a lubricious coating 534 on a proximal shaft exterior wall 533. The guiding shaft assembly 500 may optionally include a plurality of bands like the plurality of bands 444 of guiding shaft assembly 400.

The guiding shaft assembly 500 differs from the guiding shaft assembly 400 in that stiffener members 550 are disposed within the one or more side lumens 564. In addition, unlike guiding shaft assembly 400, guiding shaft assembly 500 of this example includes a collar 562. The collar 562 is located proximal of the distal tip 448. The stiffener members 550 are operatively attached to the collar 562 at a stiffener member end 554. By way of example only, the stiffener members 550 may be attached to the collar 562 with brazing, welding, or gluing. The collar 562 is configured to transfer the rigidity of the stiffener members 550 to the distal lumen 446 (see FIG. 11A-11C).

The stiffener members 550 are rigid, elongate members that may have a cross-sectional shape that is round, triangular, square, rectangular or any other suitable shape. The stiffener members 550 are configured to translate through the one or more side lumens 564. The side lumens 564 may also have a cross-sectional hollow that is round, triangular, square, rectangular or any other suitable shape that allows the translation of the stiffener members 550. The shape of the stiffener members 550 may be the same shape or a different shape than the hollow of the one or more side lumens 564. The stiffener members 550 may be solid or hollow. While two stiffener members 550 are shown in FIG. 13, guiding shaft assembly 500 may instead have only one stiffener member 550; or more than two stiffener members 550.

When the stiffener members 550 are selectively translated distally within guiding shaft assembly 500, stiffener members 550 counteract the lateral bias of the distal section and thereby vary the deflection curvature DCx, similar to the operational sequence shown in FIGS. 11A-11C. An actuator may be operatively coupled to the stiffener members 550 to translate the stiffener members 550 linearly, as discussed below. In other examples, the stiffener members 550 may be manually inserted through the one or more side lumens 564. The collar 562, combined with the rigidity of the stiffener members 550, provides a combined rigidity similar to stiffener member 450 of guiding shaft assembly 400. The combined rigidity counters the lateral bias of the distal shaft as the collar 562 is inserted to the insertion depth (e.g., like the insertion depth IDx shown in FIGS. 11A-11C), to thereby vary the deflection curvature (e.g., like the deflection curvature DCx shown in FIGS. 11A-11C). As with the guiding shaft assembly 400, the insertion depth $ID_x$ associated with guiding shaft assembly 500 is inversely related to the deflection curvature DCx.

Figures 14A, 14B:
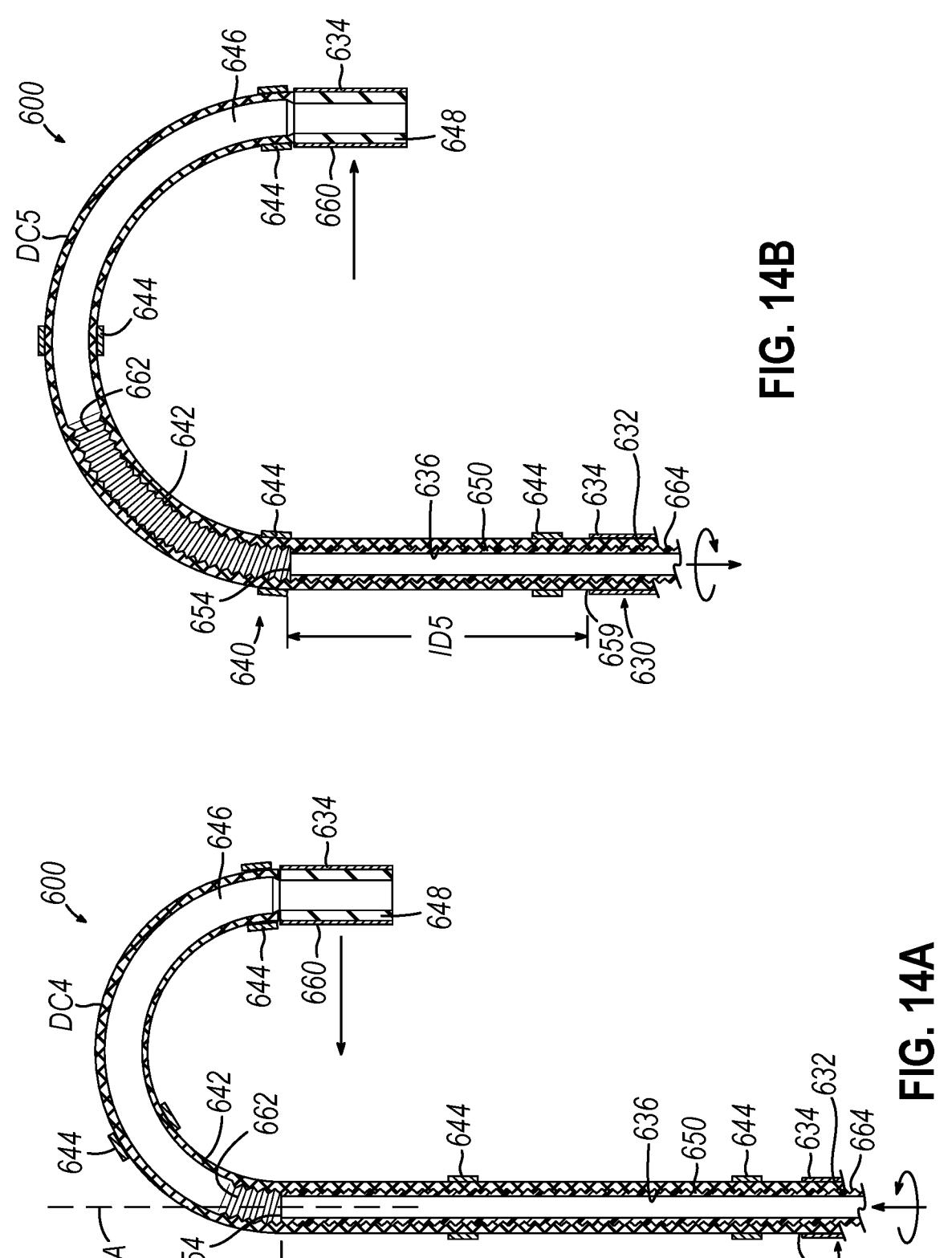
FIGS. 14A and 14B are cross-sectional views of yet another exemplary guiding shaft assembly including a first and a second helical feature for use with the guiding sheath assembly of FIG. 10, with FIG. 14A having a tighter deflection curvature relative to the deflection curvature of FIG. 14B.

C. A. Exemplary Guiding Shaft Assembly Having a First and Second Helical Feature Mated to Adjust a Deflection Curvature FIGS. 14A-14B show yet another example of a guiding shaft assembly 600, which is similar to the guiding shaft assembly 400 except for the differences noted below. The guiding shaft assembly 600 of this example includes a proximal section 630, a distal section 640, and a stiffener member 650. The proximal section 630 includes a proximal shaft 632 that defines a proximal lumen 636. The proximal section 630 may also include a lubricious coating 634. The lubricious coating 634 may be on the proximal lumen 636 or elsewhere. The distal section 640 includes a distal shaft 642 that defines a distal lumen 646, bands 644, and a distal portion 660 with an open distal tip 648.

The distal section 640 of guiding shaft assembly 600 is like the distal section 440 of guiding shaft assembly 400 in that the distal section 640 is resiliently biased to deviate laterally from the longitudinal axis LA; and the stiffener member 650 is advanced distally to increase the insertion depth IDx, which counteracts this lateral bias thereby resulting in a smaller deflection curvature DCx. Like the guiding shaft assembly 400, the insertion depth IDx for stiffener member 650 is the distance from a proximal section end 659 to the stiffener member end 654; and deflection curvature DCx is the distance from the longitudinal axis LA to the center of the distal portion 660. The distal portion 660 may also have a lubricious coating 634 similar to the guiding shaft assembly 400.

The guiding shaft assembly 600 differs from the guiding sheath assembly 400 in that stiffener member 650 is translated proximally and distally by a rotational movement of the stiffener member 650. The proximal and distal shafts 632, 642 include a first helical feature 662. The first helical feature 662 mates with a second helical feature 664 on the stiffener member 650. The first helical feature 662 may be an internal thread, and the second helical feature 664 may be an external thread, or vice versa. The first and second helical features 662, 664 may be right-hand helical features that use clockwise rotation to translate the stiffener member 650 distally or left-hand helical features that use counterclockwise rotation to translate the stiffener member 650 distally. In some other versions, rather than being in the form of complementary internal and external threading, the helical features 662, 664 may be formed as a first and second helical coil structure, respectively. In such versions, the first and second helical coil may slidably interlock with each other to form a mated arrangement that has a similarly sized inside and outside diameters. Such helical structures may be formed by laser-cutting tubes that form shafts 632, 642 and stiffener member 650; or in any other suitable fashion.

FIG. 14A shows the guiding shaft assembly 600 having a longer insertion depth ID4 relative to the insertion depth ID5 shown in FIG. 14B; and a tighter deflection curvature DC4 relative to deflection curvature DC5 shown in FIG. 14B. The stiffener member 650 may be actuated by an actuator (e.g., rotary knob, rotary dial, slider, etc.) located on the handle assembly 310; or may be directly rotated with the user's hand through insertion port 350 until the second helical feature 664 mates with the first helical feature 662. After the second helical feature 664 mates with the first helical feature 662, the stiffener member 650 or actuator rotates the stiffener member 650 in a clockwise direction in order to translate the stiffener member 650 distally. The pitch of the first and second helical features 662, 664 may be any suitable pitch as will apparent to those skilled in the art in view of the teachings herein.

FIG. 14B shows the guiding shaft assembly 600 of FIG. 14A with the stiffener member 650 rotating in a counterclockwise direction. The helical features 662, 664 have engaged each other and transitioned the stiffener member 650 in proximal direction decreasing the insertion depth ID5 relative to the insertion depth ID4 (see FIG. 14A), thereby loosening the deflection curvature DC5 relative to the deflection curvature DC4. (see FIG. 14A).

Figure 15:
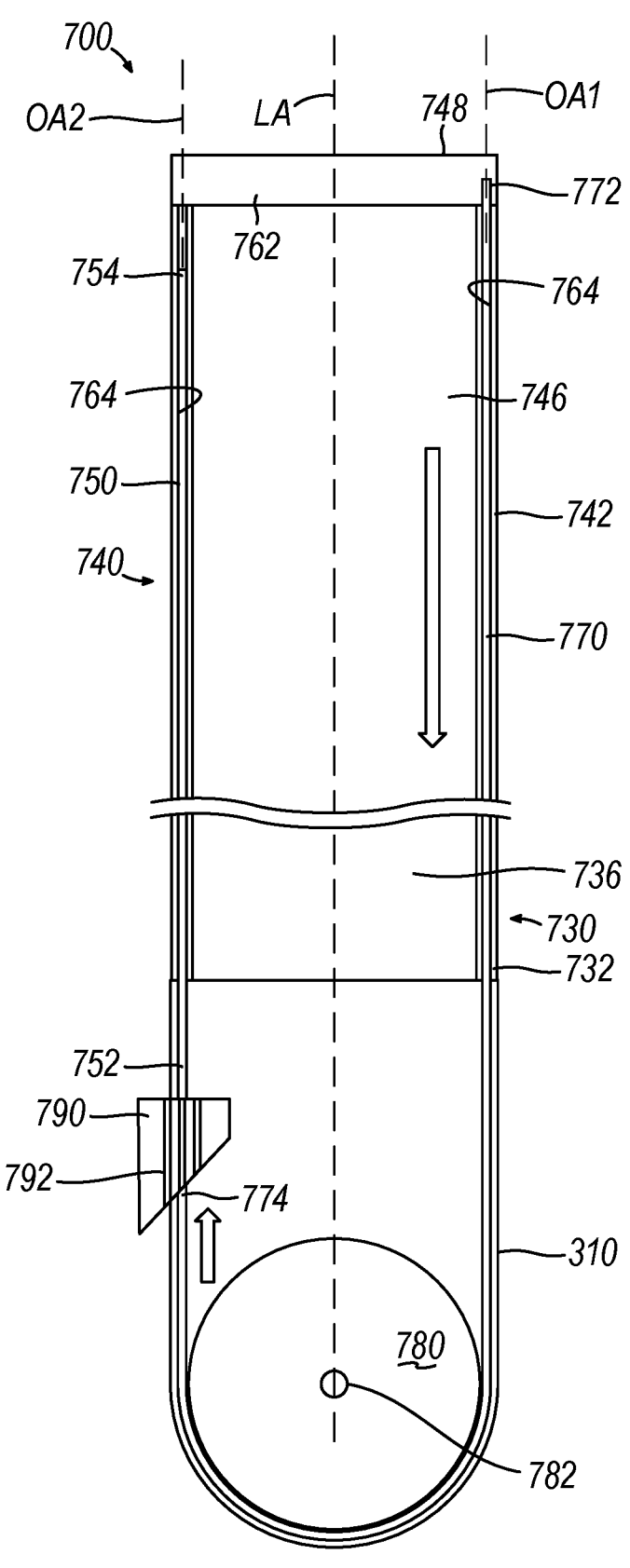
FIG. 15 is a schematic view of yet another exemplary guiding shaft assembly with the distal section in the straight position.

D. Exemplary Guiding Shaft with a Stiffener Member and a Pull Wire for Adjusting Deflection Curvature FIG. 15 shows another example of a guiding shaft assembly 700, in a straight position. The guiding shaft assembly 700 of this example is similar to the guiding shaft assembly 400, except for the differences noted below. The guiding shaft assembly 700 includes a proximal section 730, a distal section 740, and a stiffener member 750. The proximal section 730 has a proximal shaft 732, a pair of side lumens 764, and a proximal lumen 736. The distal section 740 includes a distal shaft 742, a distal lumen 746, the pair of side lumens 764, and a distal tip 748. The distal section may additionally include a plurality of bands similar to the plurality of bands 444 of guiding shaft assembly 400; and a lubricious coating similar to the lubricious coating 434 of guiding shaft assembly 400. The stiffener member 750 extends distally through one of the side lumens 764 from a proximal member end 752 to a distal member end 754.

The distal section 740 of guiding shaft assembly 700 differs from the distal section 440 of the guiding shaft assembly 400 in that the distal section 740 is not resiliently biased toward a pre-curved shape. The distal section 740 of this example may be constructed of materials such as plastic or a surgically safe metal that has malleable yet rigid properties such as braided stainless steel. In some versions, the distal section 740 may be resiliently biased to assume a straight configuration, such that distal section 740 is resiliently biased toward the longitudinal axis LA. The guiding shaft assembly 700 also differs from the guiding shaft assembly 400 in that the guiding shaft assembly 700 includes a collar 762, a pull wire 770, and a pulley 780.

The collar 762 of the present example is in the form of an annular ring operatively connected to the pull wire 770 and is configured to be acted upon by a proximal force imparted by the pull wire 770. The collar 762 may be constructed of a rigid plastic or surgically safe metal. The collar 762 is located proximal of the distal tip 748. The pull wire 770 includes a first wire end 772 and a second wire end 774. The pull wire 770 is constructed of a metal wire, polymeric fiber, or any other suitable material; and is configured to apply tension upon the collar 762. The pull wire 770 is affixed to the collar 762 at a first wire end 772 by gluing, welding, soldering, brazing, or any other suitable technique. The pull wire 770 proximally extends from the collar 762 through a first side lumen 764 along a first offset axis OA1. The first offset axis OA1 extends parallel to the longitudinal axis LA.

A portion of the pull wire 770 wraps around a perimeter of the pulley 780. The pulley 780 is located within the handle assembly 310 and may include a bearing 782. The bearing may have steel needles, ball bearings, or brass bushings or various suitable structures as will be apparent to those skilled in the art that reduce rotational friction. The pulley 780 may also be fixedly attached to the handle assembly 310 (see FIG. 10) and remain statically positioned. The pulley 780 may be lubricated or coated to reduce friction between the pull wire 770 and the pulley 780. The pulley 780 is configured to change the direction of the force administered to the pull wire 770. The pull wire 770 further extends distally from the perimeter of the pulley 780 into a second side lumen 764 that lies along the second offset axis OA2. The second offset axis OA2 is parallel to the longitudinal axis LA on a side opposite the first offset axis OA1. The pull wire 770 is operatively attached to the proximal end of an actuator 790 at the second wire end 774.

The actuator 790 is located within the handle assembly 310 and proximate to the second offset axis OA2. The actuator is operatively coupled to the proximal member end 752. The actuator may include a button, gearing, threading, cam surfaces, sliders, or other various suitable structures as will be apparent to those skilled in the art that translates a rigid body and a tensioning device. The actuator 790 may further include a detent feature (not shown) configured to hold the guiding shaft assembly 700 in a desired position, and an indicator 792 configured to provide tactile or visual feedback of the desired position. The indicator 792 may indicate the insertion depth (e.g., similar to the insertion depth IDx shown in FIGS. 11A-11C) or the deflection curvature (e.g., similar to the deflection curvature DCx shown in FIGS. 11A-11C). The actuator 790 may use a rotational, transverse, or longitudinal movement to simultaneously translate the stiffener member 750 and the pull wire 770 along the second offset axis OA2. The stiffener member 750 extends distally from a proximal member end 752 through a second side lumen (e.g., like second side lumen 464 shown in FIG. 12) to the distal member end 754. In some examples, the stiffener member 750 may be disposed within the proximal and distal lumens 736, 746.

In the straight position, the distal member end 754 is in the proximal-most location, and the first wire end 772 is in the distal-most location. The stiffener member 750 resiliently biases the portion of distal section 740 that contains the stiffener member 750 to the straight position and aligns the distal section 740 with the longitudinal axis LA.

In operation, the guiding shaft assembly 700 may be transitioned from the straight position to a first deflected position (not shown) having a minimum deflection curvature similar to deflection curvature DC1 shown in FIG. 11A; and further to a second deflected position (not shown) having a maximum deflection curvature similar to deflection curvature DC3 shown in FIG. 11C. The guiding shaft assembly 700 is transitioned to the first deflected position by a user's thumb or finger acting upon the actuator 790. The user's thumb or finger acts upon the actuator by rotating, depressing, or translating the actuator 790. The actuator 790 translates the stiffener member 750 distally along the second offset axis OA2 and simultaneously translates the second wire end 774 distally along the second offset axis OA2.

The second wire end 774 translates distally and translates the portion of the pull wire 770 located on the perimeter of pulley 780. The pulley 780 rotates around the bearing 782 and changes the distal force applied to the second wire end 774 by the actuator 790 into a proximal force that proximally translates the first wire end 772 proximally. The first wire end 772 translates the collar 762 proximally thereby transitioning the distal shaft 742 from the straight position into a first deflected position having a minimum deflection curvature similar to deflection curvature DC1 shown in FIG. 11A. The minimum deflection curvature at this stage has a shorter width relative to the maximum deflection curvature similar because the portion of the distal section 740 that does not contain the stiffener member 750 sharply deflects relative to the maximum deflection curvature. The proximal force exhibited on the collar 762 greatly overcomes the straight bias of the portion of the distal section 740 located distal of the distal member end 754.

The first deflected position is transitioned to the second deflected position by the user's finger or thumb further acting upon the actuator 790. The second deflected position has a maximum deflection curvature similar to deflection curvature DC3 shown in FIG. 11C. The actuator 790 further translates the stiffener member 750 distally while simultaneously transitioning the first wire end 772 proximally via the pulley 780. The first wire end 772 further translates the collar 762 proximally. The proximal force exhibited on the collar 762 combined with the more distally located distal member end 754 results in a maximum deflection curvature that corresponds with the force exhibited by the stiffener member 750 and the proximal force exhibited on the collar 762. The maximum deflection curvature is relatively wider than the minimum deflection curvature.

The actuator 790 may have an infinite or a finite number of positions between the first deflected position and the second deflected position. By way of example only, the actuator 790 having a finite number of positions may have the first deflected position, the second deflected position, a third deflected position. A detent may hold the guiding shaft assembly 700 in the corresponding position and the indicator 792 and may give a tactile or visual indication of the corresponding position.

While actuator 790 is described in the context of the other elements shown in FIG. 15, an actuator like actuator 790 may be used to selectively drive translation of any of the stiffener members 450, 550, 650 described above. By way of further example only, an actuator like actuator 790 may include one or more levers, sliders, threading, buttons, gears, motors, wires, pulleys or any other suitable structures as will be apparent to those skilled in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A shaft assembly, comprising: (a) a proximal section extending distally along a longitudinal axis, the proximal section including a proximal shaft defining a proximal lumen; (b) a distal section extending distally from the proximal section including a distal shaft defining a distal lumen configured to align with the proximal lumen, the distal section being configured to be biased to deflect laterally away from the longitudinal axis into a deflection curvature having a width, the distal section being configure to fit within a cardiovascular anatomical passageway; and (c) at least one stiffener member configured to selectively translate along the longitudinal axis, the at least one stiffener member being configured to counteract the lateral bias of the distal section and thereby reduce the width of the deflection curvature based on a longitudinal position of the stiffener member relative to the distal section.

Example 2

The shaft assembly of Example 1, the at least one stiffener member being disposed within the proximal lumen and being selectively translatable through the distal lumen.

Example 3

The shaft assembly of any one or more of Examples 1 through 2, the deflection curvature width ranging from approximately 0 mm to approximately 55 mm.

Example 4

The shaft assembly of Example 3, the deflection curvature width ranging from approximately 20 mm to approximately 55 mm.

Example 5

The shaft assembly of any one or more of Examples 1 through 4, the at least one stiffener member being disposed within one or more side lumens formed in the proximal and distal sections.

Example 6

The shaft assembly of any one or more of Examples 1 through 5, further including one or more pull wires operable to control lateral deflection of the distal section.

Example 7

The shaft assembly of any one or more of Examples 1 through 6, further comprising an actuator configured to selectively deflect the distal section.

Example 8

The shaft assembly of Example 7, the actuator being operable to linearly translate to linearly translate the at least one stiffener member.

Example 9

The shaft assembly of any one or more of Examples 7 through 8, the actuator being rotatable to linearly translate the at least one stiffener member.

Example 10

The shaft assembly of any one or more of Examples 1 through 9, further comprising a collar operable to control lateral deflection of the distal section.

Example 11

The shaft assembly of Example 10, the collar being attached to the at least one stiffener member.

Example 12

The shaft assembly of any one or more of Examples 10 through 11, further including one or more pull wires operable to control lateral deflection of the distal section, the collar being attached to the one or more pull wires.

Example 13

The shaft assembly of any one or more of Examples 1 through 12, further including:
   (a) one or more pull wires operable to control lateral deflection of the distal section; and
   (b) a pulley, the one or more pull wires engaging the pulley, the pulley being configured to change a direction of force administered to the one or more pull wires.

Example 14

The shaft assembly of Example 13, further comprising a collar operable to control lateral deflection of the distal section, the collar being proximal of a distal tip of the proximal shaft and the collar being affixed to the one more pull wires that extend along a first axis parallel to the longitudinal axis, a portion of the one or more pull wires wrapping around the pulley, the one or more pull wires being operable to translate through a second axis located opposite the first axis and parallel the longitudinal axis, the one or more pull wires extending distally along the second axis and being affixed to an actuator, and the actuator being affixed to the stiffener member that extends distally along the second axis.

Example 15

A sheath assembly comprising: (a) the shaft assembly of any one or more of Examples 1 through 14, the proximal and distal lumens being sized to slidably receive a catheter; and (b) a handle assembly including a proximal opening configured to receive the catheter, the shaft assembly extending distally from the handle assembly, the proximal opening being in communication with the proximal and distal lumens.

Example 16

A shaft assembly comprising: (a) a proximal shaft extending distally along a longitudinal axis and defining a proximal lumen; (b) a distal shaft being resiliently biased to deflect laterally away from the longitudinal axis, the distal shaft including a first helical feature extending distally and defining a distal lumen; and (c) one or more stiffener members including a second helical feature configured to mate with the first helical feature, the stiffener member being selectively translatable along the longitudinal axis by rotating the one or more stiffener members to reduce a deflection curvature defined by the distal shaft.

Example 17

The shaft assembly of Example 16, the first and second helical features comprising complementary interlocking helical coils.

Example 18

A shaft comprising: (a) an elongate shaft extending distally along a longitudinal axis to a distal tip, the elongate shaft defining an elongate lumen; (b) a stiffener member having a proximal end extending distally through the elongate shaft to a distal end, the stiffener member being configured to urge the elongate shaft toward the longitudinal axis; (c) a collar proximate to the distal tip; (d) a pull wire having a first end and a second end, the first end being affixed to the collar in a first axis that is parallel to the longitudinal axis and the second end being located along a second axis opposite the first axis; (e) a pulley configured to engage a portion of the pull wire between the first and second ends; and (f) an actuator attached to the second end of the pull wire and the proximal end of the stiffener member, the actuator being operable to simultaneously translate the stiffener member and second end distally along the second axis, the pulley being configured to change a distal force acted upon the second end to a proximal force at the first end, the collar being configured to translate proximally along the first axis, and the stiffener member being configured to translate distally a deflection curvature width.

Example 19

The shaft assembly of Example 18, the stiffener member being disposed within one or more side lumens formed in the elongate shaft.

Example 20

The shaft assembly of Example 19, the pull wire being disposed within the one or more side lumens.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by those skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A shaft assembly, comprising:
(a) a proximal section extending distally along a longitudinal axis of the shaft assembly, the proximal section comprising a proximal shaft defining a proximal lumen;
(b) a distal section extending distally from the proximal section, the distal section comprising a distal shaft defining a distal lumen configured to align with the proximal lumen of the proximal shaft, the distal section being configured to be biased to deflect laterally away from the longitudinal axis of the shaft assembly into a deflection curvature having a width, the distal section being configured to fit within a cardiovascular anatomical passageway; and
(c) a stiffener member assembly comprising a collar, and a first stiffener member attached at one end of the first stiffener member to an outer wall of the collar, the stiffener member assembly configured to selectively translate in a direction of the longitudinal axis such that the collar translates within the proximal lumen or the distal lumen and the first stiffener member translates within a first side lumen in the proximal shaft and the distal shaft, the first side lumen being off-axis relative to the proximal lumen and the distal lumen, the first stiffener member being configured to counteract the lateral bias of the distal section and thereby reduce the width of the deflection curvature based on a longitudinal position of the first stiffener member relative to the distal section.

2. The shaft assembly of claim 1, the width of the deflection curvature ranging from approximately 0 mm to approximately 55 mm.

3. The shaft assembly of claim 2, the width of the deflection curvature ranging from approximately 20 mm to approximately 55 mm.

4. The shaft assembly of claim 1, further comprising one or more second stiffener members attached to the outer wall of the collar, and one or more second side lumens in the proximal section and the distal section, each of the one or more second stiffener members being disposed within a corresponding one of the one or more second side lumens in the proximal section and the distal section.

5. The shaft assembly of claim 4, further comprising an actuator coupled to the first stiffener member and the one or more second stiffener members, the longitudinal position comprising two or more different longitudinal positions, and the actuator being configured to move the one or more second stiffener members between the two or more different longitudinal positions.

6. The shaft assembly of claim 1, further including one or more pull wires operable to control the lateral deflection of the distal section.

7. The shaft assembly of claim 1, further comprising an actuator configured to selectively deflect the distal section.

8. The shaft assembly of claim 7, the actuator being operable to linearly translate the first stiffener member.

9. The shaft assembly of claim 7, the actuator being rotatable to linearly translate the first stiffener member.

10. The shaft assembly of claim 1, further including one or more pull wires operable to control the lateral deflection of the distal section, the collar being attached to the one or more pull wires.

11. The shaft assembly of claim 1, further comprising:
(a) one or more pull wires operable to control the lateral deflection of the distal section; and
(b) a pulley, the one or more pull wires engaging the pulley, the pulley being configured to change a direction of force administered to the one or more pull wires.

12. The shaft assembly of claim 11, the collar being proximal of a distal tip of the proximal shaft and the collar being affixed to the one or more pull wires that extend along a first axis parallel to the longitudinal axis, a portion of the one or more pull wires wrapping around the pulley, the one or more pull wires being operable to translate through a second axis located opposite the first axis and parallel to the longitudinal axis, the one or more pull wires extending distally along the second axis and being affixed to an actuator, and the actuator being affixed to the first stiffener member.

13. A sheath assembly comprising:
(a) the shaft assembly of claim 1, the proximal lumen and the distal lumen being sized to slidably receive a catheter; and
(b) a handle assembly including a proximal opening configured to receive the catheter, the shaft assembly extending distally from the handle assembly, the proximal opening being in communication with the proximal lumen and the distal lumen.

14. The shaft assembly of claim 1, further comprising an actuator coupled to the first stiffener member, the longitudinal position comprising two or more different longitudinal positions, and the actuator being configured to move the first stiffener member between the two or more different longitudinal positions.

15. The shaft assembly of claim 14, the two or more different longitudinal positions comprising at least three different longitudinal positions, each of the at least three different longitudinal positions resulting in a different width of the deflection curvature corresponding to a respective one of the at least three different longitudinal positions.

\* \* \* \* \*